United States Patent

Ashton et al.

[11] Patent Number: 5,833,678
[45] Date of Patent: *Nov. 10, 1998

[54] ABSORBENT ARTICLE HAVING IMPROVED DRY/WET INTEGRITY

[75] Inventors: Gregory Ashton, Higashinada-ku, Japan; John Thomas Cooper, West Chester; Craig Andrew Hawkins, Maineville, both of Ohio

[73] Assignee: The Procter & Gamble Company, Cincinnati, Ohio

[ * ] Notice: The term of this patent shall not extend beyond the expiration date of Pat. No. 5,387,208.

[21] Appl. No.: 589,522

[22] Filed: Jan. 22, 1996

Related U.S. Application Data

[63] Continuation of Ser. No. 268,351, Jun. 30, 1994, which is a continuation of Ser. No. 97,634, Jul. 26, 1993, Pat. No. 5,387,208.

[51] Int. Cl.⁶ .................................................. A61F 13/15
[52] U.S. Cl. ........................ 604/378; 604/366; 604/370; 604/372
[58] Field of Search ..................... 604/358, 378, 604/379, 380, 365, 366, 370, 372, 385.1

[56] References Cited

U.S. PATENT DOCUMENTS

| | | |
|---|---|---|
| 3,911,173 | 10/1975 | Sprague, Jr. . |
| 3,994,299 | 11/1976 | Karami ..................... 604/378 |
| 4,195,634 | 4/1980 | DiSalvo et al. ........................ 128/290 |
| 4,522,863 | 6/1985 | Keck et al. . |
| 4,526,577 | 7/1985 | Schmidt et al. ....................... 604/366 |
| 4,573,986 | 3/1986 | Minetola et al. . |
| 4,673,402 | 6/1987 | Weisman et al. . |
| 4,710,185 | 12/1987 | Sneyd et al. . |
| 4,785,996 | 11/1988 | Ziecker et al. . |
| 4,806,408 | 2/1989 | Pierre et al. ............................... 428/76 |
| 4,842,666 | 6/1989 | Werenicz . |
| 4,891,249 | 1/1990 | McIntyre . |
| 5,024,667 | 6/1991 | Malcolm et al. . |
| 5,137,537 | 8/1992 | Herron et al. . |
| 5,145,689 | 9/1992 | Allen et al. . |
| 5,151,092 | 9/1992 | Buell et al. . |
| 5,190,533 | 3/1993 | Blackburn ............................... 604/378 |
| 5,217,445 | 6/1993 | Young et al. . |
| 5,387,208 | 2/1995 | Ashton et al. .......................... 604/358 |

FOREIGN PATENT DOCUMENTS

| | | |
|---|---|---|
| WO 91/11163 | 8/1991 | WIPO . |
| WO 93/11726 | 6/1993 | WIPO . |

OTHER PUBLICATIONS

Hot Melt Systems; J and M Laboratories, Inc.

*Primary Examiner*—John G. Weiss
*Assistant Examiner*—Dennis Ruhl
*Attorney, Agent, or Firm*—David M. Weirich; Steven W. Miller; Jacobus C. Rasser

[57] ABSTRACT

Disclosed is an absorbent article having a liquid pervious topsheet, a liquid impervious backsheet joined to the topsheet, and an absorbent core positioned therebetween, in which the absorbent core is enveloped by a primary core integrity layer comprising a continuous mesh of strands of thermoplastic material which is joined to the topsheet and/or the backsheet. The primary core integrity layer is particularly useful for improving the wet integrity of absorbent cores comprising an upper acquisition/distribution layer and a lower storage layer.

8 Claims, 3 Drawing Sheets

ABSORBENT ARTICLE HAVING IMPROVED DRY/WET INTEGRITY

This application is a continuation of application Ser. No. 08/268,351, filed Jun. 30, 1994, now abandoned, which is a continuation of application Ser. No. 08/097,634, filed Jul. 26, 1993, now U.S. Pat. No. 5,387,208.

FIELD OF THE INVENTION

The present invention relates to absorbent articles, e.g., diapers, incontinence garments, feminine hygiene articles, and the like, having absorbent cores with improved integrity. More particularly, the present invention relates to such absorbent articles having a primary core integrity layer comprising a continuous mesh of strands of thermoplastic material to impart dry, and particularly wet, integrity to the absorbent core and article. The invention is particularly useful for thin absorbent articles in which the absorbent core comprises an acquisition/distribution layer and a storage layer.

BACKGROUND OF THE INVENTION

Absorbent articles such as diapers which employ relatively thin absorbent cores and which are, therefore, relatively thin products, are desired for numerous reasons. For example, thinner diapers are less bulky to wear and fit better under clothing. They are also more compact in the package, making the diapers easier for the consumer to carry and store. Compactness in packaging also results in reduced distribution costs for the manufacturer and distributor.

The improvement in absorbency provided by incorporation of absorbent gelling material (hereinafter alternatively referred to as "AGM" or, in the plural, "AGMs") in absorbent cores has permitted the realization of relatively thin absorbent articles. For example, absorbent structures wherein AGMs in particulate form are incorporated into fibrous webs is disclosed in Weisman et al., U.S. Pat. No. 4,610,678, issued Sep. 9, 1986; U.S. Pat. No. 4,765,780, issued Aug. 23, 1988 to Angstadt; and U.S. Pat. No. 4,673,402, Weisman et al., issued Jun. 16, 1987.

More recently, absorbent structures have been suggested to provide improved fluid acquisition and distribution in absorbent cores. For example, U.S. Pat. No. 4,935,022, issued Jun. 19, 1990 to Lash et al.; U.S. Pat. No. 5,217,445, issued to Young et al. on Jun. 8, 1993; and International Publication No. WO/91/11163, published on Aug. 8, 1991, each disclose disposable absorbent articles having a layered absorbent core comprising an upper layer of stiffened, twisted, curled cellulose fibers and a lower storage layer.

Although the foregoing structures provide improved absorbency when incorporated into absorbent articles, it has been found that such cores tend to suffer from absorbent core slumping, cracking (i.e., breaking), and/or roping in processing, storage, and/or use. As a result, the absorption characteristics of the absorbent core are decreased such that leakage of the article incorporating the same occurs. This tendency to slump, crack, and/or rope is more likely as the absorbent core becomes thinner, for example, in the foregoing constructions incorporating AGM and/or stiffened, twisted, curled cellulosic fibers. Thin constructions particularly suffer from breakage and slumping which are believed to be due to the presence of stiffened, twisted, curled cellulosic fibers, a relatively high AGM concentration, and/or or the force typically used in packaging of the absorbent article. Breakage tends to occur along the fold lines typically imparted for packaging of the absorbent articles (e.g., in the crotch region). When such breakage occurs, the transport of fluids throughout the absorbent core is impeded. For example, where substantial breakage occurs along the crotch fold line, the rear portion of the absorbent article tends to be substantially unavailable for fluid absorption. Thus, when the front portion of the article is saturated to its absorption capacity, leakage may occur.

The tendency to slump, crack and/or rope is particularly exaggerated in absorbent cores incorporating acquisition/distribution components comprising stiffened, twisted, curled cellulose fibers such as described in the foregoing patents. On the one hand, the relatively low density of such components makes the component more likely to lose its integrity. In addition, when this component is wetted, the fibers tend to pull apart (spring back). In addition, the acquisition/distribution component tends to separate and/or slip away from other layers of the absorbent core (e.g., the storage layer) such that fluid transport from the acquisition/distribution layer to such other layers is hindered.

It is known to use glues in absorbent articles to improve absorbent core integrity. For example, U.S. Pat. No. 4,573,986, issued to Minetola et al. on Mar. 4, 1986 discloses garments in which the liquid permeable lamina and absorbent core are bonded together in face to face relation with an open pattern of adhesive. Minetola discloses that particular laminae are adhesively secured together with particular patterns, quantities, and types of adhesives to achieve faster absorbency, less absorbent core slumping, cracking and roping, and increased tensile strength without substantially reducing either the softness or overall absorbency of the garment.

While the art has solved some of the problems related to absorbent core integrity of laminated absorbent articles, it has not solved the problems to the extent nor in the manner of the present invention, particularly with respect to the integrity of thin diaper configurations having a relatively high AGM concentration, more particularly such thin diapers incorporating an acquisition/distribution layer such as those incorporating the above described chemically stiffened, twisted, curled cellulosic fibers.

The glues used to bond the absorbent core to a chassis component (i.e., topsheet or backsheet) tend to have inadequate adhesion to the cellulose fibers which are typically used in the absorbent core when the absorbent article is subjected to the dynamic motions of the wearer. As a result, the glue tends to be insufficient to maintain the integrity of the absorbent core when absorbent articles incorporating the same are in use. In other words, the absorbent core is not physically stabilized, e.g., longitudinally and/or laterally, in the absorbent article. The loss of adhesion and integrity is particularly exaggerated when the article is wetted. For example, when the AGM and cellulose fibers typically incorporated into the absorbent core component expand upon wetting, the forces exerted by the expanding AGM and cellulose fibers tend to cause a loss of adhesion between the AGM, fibers, and the glue.

In addition, when absorbent core/chassis glues are applied in a spray application to form beads and/or spirals for bonding of the laminae, the bonding is relatively localized. Thus, although the amount of glue is relatively great, this method of application leaves a large portion of the absorbent core surface unbonded and free to move.

As a result of this inadequate adhesion and/or localized bonding, the absorbent core tends to slump, crack and/or rope such that absorption by the absorbent article is diminished.

It is an object of the present invention to provide an absorbent structure, particularly a thin absorbent structure, having dry and wet integrity. Thus it is an object of the present invention to provide such absorbent structures having a reduced tendency to break, slump, and/or rope while dry or wet. Another object of the present invention is to provide absorbent articles, particularly thin absorbent articles, in which the absorbent core and/or layer thereof is enveloped by a continuous mesh of strands of thermoplastic material. It is a further object of this invention to provide such absorbent articles wherein the absorbent core can acquire fluid rapidly in the region of discharge and transport the fluid over a relatively large proportion of an absorbent core storage area and, additionally, be capable of effectively acquiring and distributing discharged bodily fluid from second or other successive voidings.

SUMMARY OF THE INVENTION

The present invention relates to an absorbent article having a liquid pervious topsheet, a liquid impervious backsheet joined to the topsheet, an absorbent core positioned therebetween, and a primary core integrity layer formed of a continuous mesh of strands of thermoplastic material positioned between the absorbent core and a chassis component or between layers of a multilayer absorbent core to provide improved absorbent core integrity, especially when wet. The primary core integrity layer imparts structural integrity to the absorbent core without requiring a great amount of material and without substantially reducing either the softness, flexibility, or absorbency of the absorbent article.

In a preferred embodiment of the present invention, the primary core integrity layer envelopes at least a portion of at least one edge, preferably at least a portion of each of the side edges, of the absorbent core or layer thereof between a chassis component and the primary core integrity layer. The primary core integrity layer in this embodiment is preferably directly joined to the chassis component.

In a particularly preferred embodiment of the present invention, the absorbent core comprises multiple absorbent layers (i.e., a multilayer absorbent core) with the primary core integrity layer enveloping the absorbent core as described above, and at least one additional core integrity layer (a secondary core integrity layer) positioned between two of the absorbent layers of the absorbent core. In a preferred configuration, the multilayer absorbent core comprises an upper acquisition/distribution layer, a lower storage layer, and a tissue layer positioned between the acquisition/distribution layer and the storage layer, the primary core integrity layer being positioned between the storage layer and the backsheet and directly joined to the topsheet and the secondary core integrity layer being positioned between the acquisition/distribution layer and the tissue layer.

The primary core integrity layer (and any optional secondary core integrity layer) is formed from a thermoplastic material, preferably a hot-melt adhesive, such that it can be readily formed on-line during construction of the absorbent article. In alternative embodiments, the thermoplastic material can be an elastomeric, pressure-sensitive, and/or high wet strength hot-melt adhesive. Elastomeric adhesives tend to be flexible such that there is a reduced tendency for adhesive and/or cohesive failure of the bonds effecting joinder in the article (relative to non-elastomeric adhesives). As a result, the absorbent core has an enhanced tendency to remain in place and/or to retain its integrity. Pressure-sensitive adhesives (further) reduce the tendency of absorbent core components adjacent the primary or secondary core integrity layers to separate from other absorbent article components, and are particularly effective in reducing slippage/separation of the acquisition/distribution layer from the storage layer. For a given strand denier, high wet strength adhesives tend to provide greater adhesion to wetted cellulosic fibers than other, non-high wet strength adhesives to provide enhanced wet integrity.

DESCRIPTION OF PREFERRED EMBODIMENTS

1. Introduction

The present invention relates to absorbent articles, such as diapers, training pants, sanitary napkins, adult incontinence devices, and the like, that have an absorbent core and a primary core integrity layer that provides improved dry and wet integrity to the absorbent core and to the absorbent article.

The term "absorbent article" refers to devices which absorb and contain body exudates, and, more specifically, refers to devices which are placed against or in proximity to the body of the wearer to absorb and contain the various exudates discharged from the body. While the following is directed to a diaper, it should be understood that the present invention is also applicable to other absorbent articles such as incontinent briefs, incontinent undergarments, training pants, diaper holders and liners, feminine hygiene garments, feminine hygiene products such as sanitary napkins and pantiliners, and the like.

As used herein, the term "diaper" refers to an absorbent article generally worn by infants and incontinent persons that is worn about the lower torso of the wearer.

Figure 1:
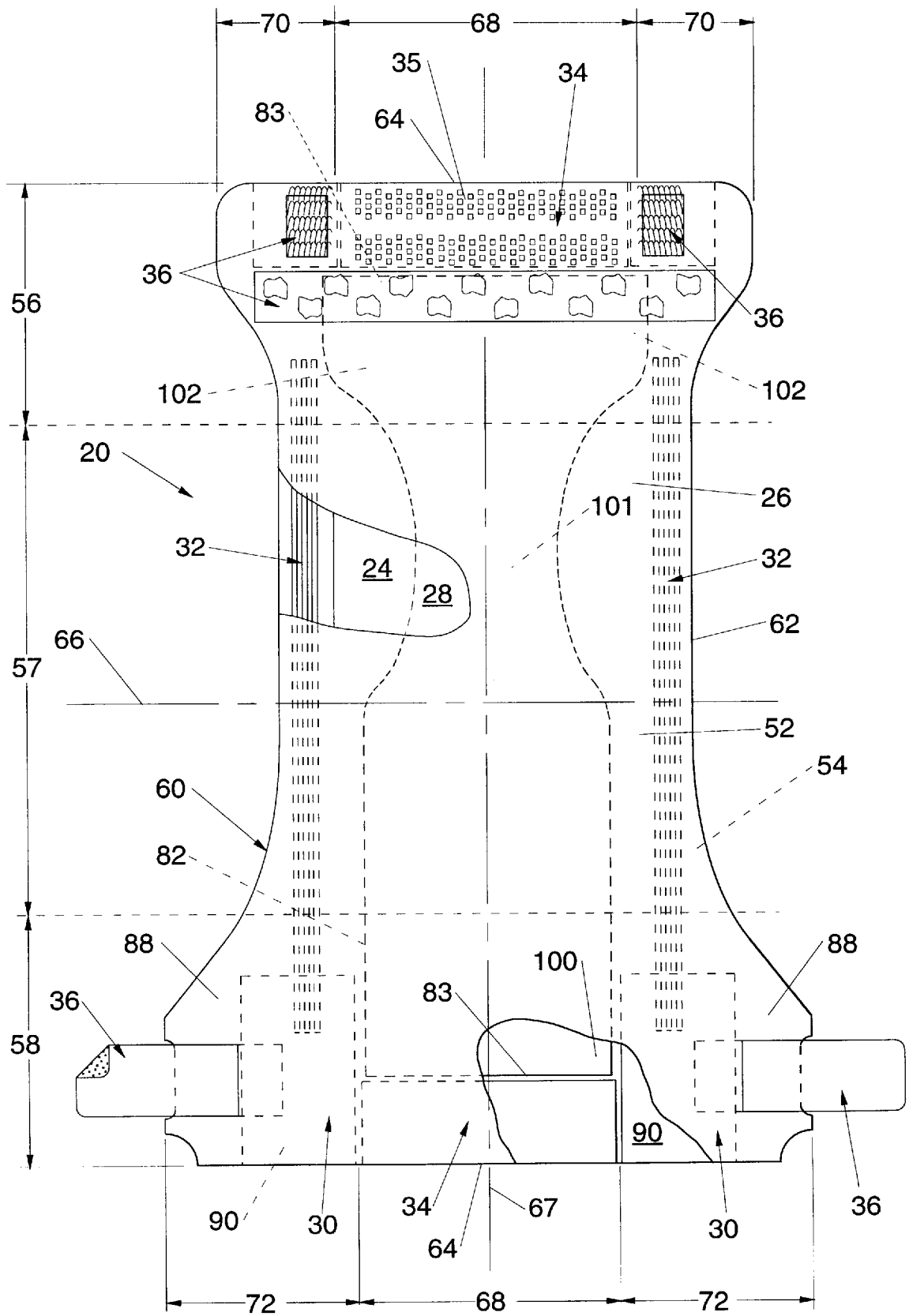
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface, oriented towards the viewer. As shown in FIG. 1, the diaper 20 preferably comprises a liquid pervious topsheet 24; a liquid impervious backsheet 26 joined with the topsheet 24; an absorbent core 28 positioned between the topsheet 24 and the backsheet 26, the absorbent core 28 having a garment facing surface 100, a body facing surface 101, side edges 82, waist edges 83, and ears 102. The diaper 20 preferably further comprises elasticized side panels 30; elasticized leg cuffs 32; an elastic waist feature 34; and a fastening system generally multiply designated as 36.

The diaper 20 is shown in FIG. 1 to have an outer surface 52, an inner surface 54 opposed to the outer surface 52, a first waist region 56, a second waist region 58, a crotch region 57 positioned between the first waist region 56 and second waist region 58, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e., the inner surface 54 generally is formed by at least a portion of the topsheet 24 and other components that may be joined to the topsheet 24). The outer surface 52 comprises that portion of the diaper 20 which is positioned away from the wearer's body (i.e., the outer surface 52 generally is formed by at least a portion of the backsheet 26 and other components that may be joined to the backsheet 26). (As used herein, the portion of the diaper 20 or component thereof which faces the wearer is also referred to as the body facing surface. Similarly, the portion facing away from the wearer is also referred to herein as the garment facing surface.) Both the first waist region 56 and the second waist region 58 comprise a central region 68 and a pair of side panels which typically comprise the outer lateral portions of the waist regions. The side panels positioned in the first waist region 56 are designated 70 while the side panels in the second waist region 58 are designated 72.

FIG. 1 shows a preferred embodiment of the diaper 20 in which the topsheet 24 and the backsheet 26 have length and width dimensions generally larger than those of the absorbent core 28. The elasticized leg cuffs 32 and the backsheet 26 extend beyond the edges of the absorbent core 28 to thereby form the periphery 60 of the diaper 20. While the topsheet 24, the backsheet 26, and the absorbent core 28 may be assembled in a variety of well known configurations, preferred diaper configurations are described generally in U.S. Pat. No. 3,860,003; issued to Buell on Jan. 14, 1975; and U.S. Pat. Nos. 5,151,092 and 5,221,274, both issued to Buell et al. on Sep. 29, 1992 and Jun. 22, 1993, respectively; each of which is incorporated herein by reference. Alternatively preferred configurations for disposable diapers herein are also disclosed in U.S. Pat. No. 4,808,178; issued to Aziz et al. on Feb. 28, 1989; U.S. Pat. No. 4,695,278; issued to Lawson on Sep. 22, 1987; U.S. Pat. No. 4,795,454; issued to Dragoo on Jan. 3, 1989; U.S. Pat. No. 4,816,025; issued to Foreman on Mar. 28, 1989; and U.S. Pat. No. 5,026,364; issued Jun. 25, 1991 to Robertson. These patents are incorporated herein by reference.

Figure 2:
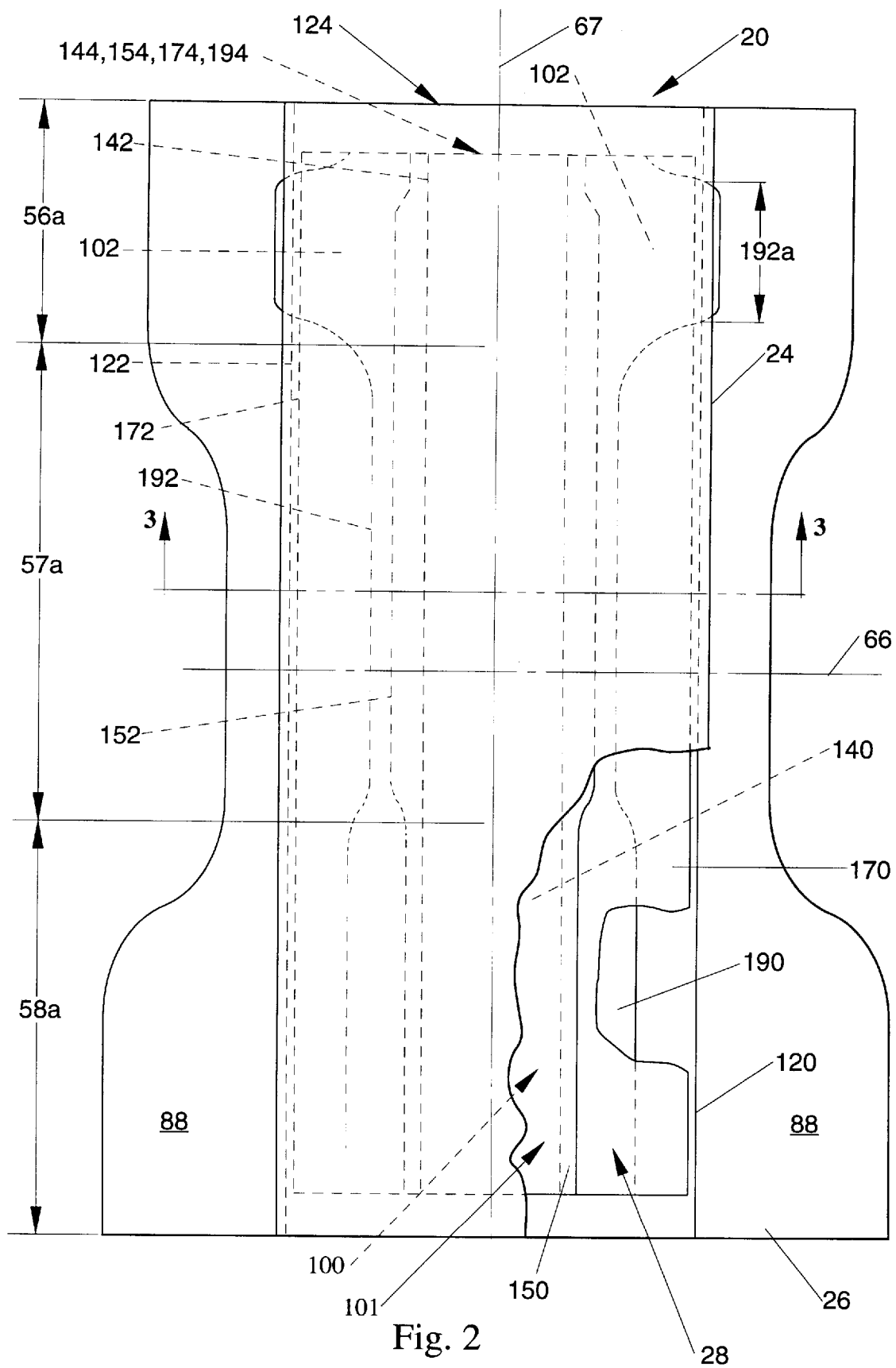
FIG. 2 is a simplified view of the diaper of FIG. 1 but containing a multiple layer absorbent core according to the present invention and having portions thereof cut-away to reveal additional underlying structure, the inner surface of the diaper facing the viewer.

FIG. 2 is a simplified view of diaper 20 as viewed from the opposite, body facing side. In FIG. 2, the elasticized side panels 30; elasticized leg cuffs 32; elastic waist feature 34; and fastening system 36 are removed for simplification.

As shown in FIG. 2, the diaper 20 contains, positioned between topsheet 24 and backsheet 26, a preferred absorbent core 28 comprising a storage layer 190, tissue layer 170, and acquisition/distribution layer 150. As shown in FIG. 2, the absorbent core 28 has a first waist region 56a, a second waist region 58a, and a crotch region 57a. The first waist region 56a is typically positioned at the end of the diaper 20 that would be covering the front of the wearer when the diaper is in use (the second waist region 58a would be at the back of the user).

Referring to FIG. 2, the storage layer 190 has a modified hour-glass shape to provide enhanced fit and reduce in-use leakage. More specifically, the storage layer 190 has ears 102 in the first waist region 56a and a substantially rectangular shape in the crotch region 57a and the second waist region 58a. The acquisition/distribution layer 150 is irregularly shaped, being substantially rectangular but having a greater width in the absorbent core crotch region 57a than at the ends 154.

As shown in FIG. 2, acquisition/distribution layer 150 has side edges 152 and end edges 154, tissue layer 170 has side edges 172 and end edges 174, and storage layer 190 has side edges 192 and end edges 194, the foregoing side edges and end edges forming the periphery of the respective layer. The width of acquisition/distribution layer 150 (lateral distance between the side edges 152) in the absorbent core crotch region 57a is slightly greater than the width at the end edges 154 (the acquisition/distribution layer 150 can be rectangular, however, since the waist regions typically do not require absorption characteristics to the extent of the crotch region, cost savings can be achieved by using less material in the waist regions). The lateral distance between the side edges 192 in the region of the ears 102 is greater than the lateral distance between the remaining portion of the side edges 192 of the storage layer 190. This configuration allows wider elasticized side panels 30 in the second waist region 58 (neither shown in FIG. 2).

In FIG. 2, the side edges 152 of acquisition/distribution layer 150 are inside the side edges 192 of the storage layer 190, which side edges 192 are inside the side edges 172 of tissue layer 170. As shown, the acquisition/distribution layer 150 has a smaller surface area than storage layer 190, which in turn has a smaller surface area than tissue layer 170. Preferably, there is a margin from the side edges 152 of the acquisition/distribution layer to the side edges 192 of the storage layer of at least about 0.5 cm in the regions proximate to where fluid is discharged during use. In diapers, this would generally correspond, for example, to the absorbent core crotch region 57a of FIG. 2, particularly at the narrowest part of the storage layer 190 in the absorbent core crotch region 57a. Additionally, especially for absorbent articles to be worn by males, such a margin is maintained in the area to be worn on the front of the wearer, typically the absorbent core first waist region 56a.

FIG. 2 also shows a primary core integrity layer 120 positioned between the backsheet 26 and the storage layer 190 and a secondary core integrity layer 140 positioned between the acquisition/distribution layer 150 and the tissue layer 170.

As shown in FIG. 2, the primary core integrity layer 120 is rectangular shaped and has side edges 122 and end edges 124 which form the periphery of primary core integrity layer 120. The secondary core integrity layer 140 is rectangular-shaped, having side edges 142 and end edges 144 which form the periphery of the secondary core integrity layer.

In FIG. 2, secondary core integrity layer 140, acquisition/distribution layer 150, tissue layer 170 and storage layer 190 are of the same (longitudinal) length, the length of these layers being less than that of topsheet 24, backsheet 26 and primary core integrity layer 120, these latter layers being of equal length. As shown in FIG. 2, the primary core integrity layer 120 envelopes at least a longitudinal portion of the acquisition/distribution layer side edges 152, tissue layer side edges 172 and storage layer side edges 192. The side edges 142 of the secondary core integrity layer 140 are positioned inside the side edges 152 of the acquisition/distribution layer 150 and inside the side edges 172 of the tissue layer 170.

Figure 3:
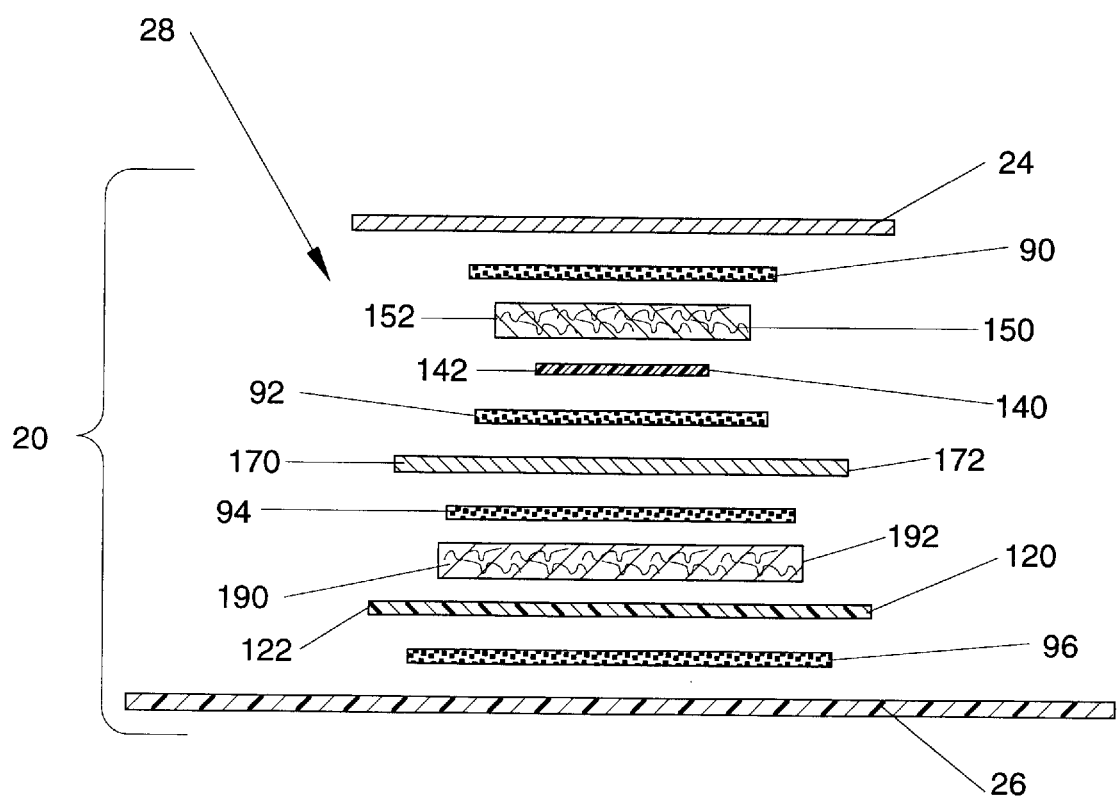
FIG. 3 is a cross-sectional view taken along line 3—3 of FIG. 2.

FIG. 3 is a cross-sectional view of the diaper 20 taken along section line 3—3 of FIG. 2. In addition to showing the core integrity layers 120 and 140 and absorbent core layers 150, 170, and 190 of FIG. 2, FIG. 3 shows construction adhesive layers 90, 92, 94, and 96.

As shown in FIG. 3, the secondary core integrity layer 140 is joined to the tissue layer 170 by construction adhesive layer 92. The secondary core integrity layer 140 is positioned adjacent the acquisition/distribution layer 150. In an alternative embodiment, the secondary core integrity layer 140 may be joined to the tissue layer 170 by the hot-melt or pressure-sensitive properties of a suitable secondary core integrity layer 140 material.

As further shown in FIG. 3, the tissue layer 170 is joined to the storage layer 190 by construction adhesive layer 94. The primary core integrity layer 120 is positioned adjacent the storage layer 190. As further shown in FIG. 3, the acquisition/distribution layer 150 is joined to the topsheet 24 by construction adhesive layer 90. The primary core integrity layer 120 is joined to the backsheet 26 by construction adhesive layer 96, and to the topsheet 24 by the hot-melt or pressure-sensitive properties of a suitable primary core integrity layer 120 material and/or by a construction adhesive (not shown). In an alternative embodiment, the primary core integrity layer 120 may be joined to the backsheet 26 by the hot-melt or pressure-sensitive properties of a suitable primary core integrity layer 120 material.

As shown in FIG. 3, construction adhesive layer 90 extends outside the side edges 152 of the acquisition /distribution layer 150 and inside the side edges 172 of tissue layer 170. Construction adhesive layer 90 can be wider than the tissue layer 170 so as to cause or enhance joinder of the primary core integrity layer 120 to the topsheet 24. However, for economic reasons a separate application of a construction adhesive will usually be made to effect such joinder. Construction adhesive layer 92 is shown in FIG. 3 to extend in the same manner as construction adhesive layer 90. Construction adhesive layer 94 extends inside the side edges 192 of the storage layer 190, and for economic reasons preferably extends a maximum lateral distance of up to about the narrowest width of the storage layer 190 in the absorbent core crotch region 57a. As shown in FIG. 3, construction adhesive layer 96 extends inside the side edges 122 of the primary core integrity layer 120. Construction adhesive layer 96 may alternatively extend outside the side edges 122 of primary core integrity layer 120 in order to cause or enhance joinder of backsheet 26 to the topsheet 24. In a preferred embodiment, construction adhesive layers 90, 92, 94, and 96 are applied over the entire length (not shown) of at least one of the acquisition/distribution layer 150, tissue layer 170, storage layer 190, backsheet 26, or topsheet 24.

2. Individual Components of the Absorbent Article

A. The Backsheet

As shown in FIGS. 2–3, the backsheet 26 is positioned adjacent the garment facing surface of the primary core integrity layer 120. (In an alternative embodiment wherein the primary core integrity layer is otherwise positioned in the absorbent article as described herein, the backsheet is positioned adjacent the garment facing surface of the absorbent core 28). The backsheet can be joined to the primary core integrity layer (or to the absorbent core as applicable) and to the topsheet by attachment means such as those well known in the art of absorbent core/chassis bonding. (As used herein, the term "joined" encompasses configurations whereby an element is directly secured to the other element by affixing the element directly to the other element (directly joined), and configurations whereby the element is indirectly secured to the other element by affixing the element to intermediate member(s) which in turn are affixed to the other element.) For example, the backsheet 26 may be secured to the primary core integrity layer 120 or to the absorbent core 28 by a uniform continuous layer of construction adhesive, a patterned layer of construction adhesive, or an array of separate lines, spirals, or spots of construction adhesive. Construction adhesives which have been found to be satisfactory are manufactured by H. B. Fuller Company of St. Paul, Minn. and specified as HL-1258, or those manufactured by Findley Adhesives, Inc. of Wauwatosa, Wis. and designated as H4003 and H2120. The attachment means can comprise an open pattern network of filaments of construction adhesive as is disclosed in U.S. Pat. No. 4,573,986, issued to Minetola et al. on Mar. 4, 1986; or several lines of construction adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. The construction adhesive can be applied by a meltblown or spray process, including a process as described herein for making the primary core integrity layer. In an alternative embodiment, the backsheet 26 may be joined to the primary core integrity layer and/or to the topsheet by the pressure-sensitive and/or hot-melt adhesive properties of a suitable primary core integrity layer material. The attachment means may alternatively comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is manufactured from a flexible liquid impervious material. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may permit vapors to escape from the absorbent core 28 (i.e., breathable) while still preventing exudates from passing through the backsheet 26.

The backsheet 26 may comprise a woven or nonwoven material, polymeric films such as thermoplastic films of polyethylene or polypropylene, or composite materials such as a film-coated nonwoven material. Preferably, the backsheet is a thin plastic film, more preferably a thermoplastic film having a thickness of from about 0.012 mm (0.5 mil) to about 0.051 mm (2.0 mils). Exemplary backsheet materials include RR8220 blown films and RR5475 cast films as manufactured by Tredegar Industries, Inc. of Terre Haute, Ind. The backsheet 26 can be embossed and/or matte finished to provide a more clothlike appearance.

B. The Topsheet

As shown in FIGS. 2–3, the topsheet 24 is positioned adjacent the body facing surface of the absorbent core 28. (In an alternative embodiment wherein the primary core integrity layer is positioned adjacent the body facing side of the absorbent core 28, the topsheet may be positioned adjacent the primary core integrity layer). The topsheet 24 is preferably joined to the absorbent core 28 (alternatively to the primary core integrity layer) and to the backsheet 26 by attachment means such as those well known in the art. Suitable attachment means are described with respect to joining the backsheet 26 to the primary core integrity layer 120.

The topsheet 24 is compliant, soft feeling, and non-irritating to the wearer's skin. Further, the topsheet 24 is liquid pervious, permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 may be made of a hydrophobic material to isolate the wearer's skin from liquids contained in the absorbent core 28. The topsheet may be formed from one or more layers of materials, for example, one or more layers of the foregoing materials. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

C. The Absorbent Core

The absorbent core 28 may be any absorbent means which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials or any equivalent material or combinations of materials. The configuration and construction of the absorbent core may also be varied (e.g., the absorbent core may have varying caliper zones, a hydrophilic gradient, an absorbent gelling material gradient, or lower average density and lower average basis weight acquisition zones; or may comprise one or more layers or structures, i.e., members, including sheets or webs. In addition, each member need not be formed of a single unitary piece of material, but may be formed of a number of smaller strips or components joined together lengthwise or width-wise, as long as they are in fluid communication with one another.) The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

Exemplary absorbent structures for use as the absorbent core 28 are described in U.S. Pat. No. 4,610,678, issued to Weisman et al. on Sep. 9, 1986; U.S. Pat. No. 4,673,402, issued to Weisman et al. on Jun. 16, 1987; U.S. Pat. No. 4,765,780, issued to Angstadt on Aug. 23, 1988; U.S. Pat. No. 4,888,231, issued to Angstadt on Dec. 19, 1989; and U.S. Pat. No. 4,834,735, issued to Alemany et al. on May 30, 1989. The disclosure of each of these patents is incorporated herein by reference. In a preferred embodiment, the absorbent core comprises a dusting layer, e.g., as described in the above referenced U.S. Pat. Nos. 4,888,231 and 4,765,780.

The absorbent core preferably comprises an absorbent member comprising at least one fibrous web or batt which comprises entangled masses of hydrophilic fibers and which may also comprise particles of AGM.

Any type of hydrophilic fibrous material which is suitable for use in conventional absorbent products is suitable for use in the absorbent member. Specific examples of such hydrophilic fibrous materials include cellulose fibers, modified cellulose fibers, rayon, polyester fibers such as polyethylene terephthalate (DACRON), hydrophilic nylon (HYDROFIL), and the like. Other examples of suitable hydrophilic fibrous materials include hydrophilized hydrophobic fibers, such as surfactant-treated or silica-treated thermoplastic fibers derived, for example, from polyolefins such a s polyethylene or polypropylene, polyacrylics, polyamides, polystyrenes, polyurethanes and the like. For reasons of availability and cost, cellulose fibers, in particular airfelt, are preferred for use in the absorbent core, particularly the storage layer described herein.

Suitable cellulosic fiber materials include the stiffened, twisted, curled, cellulosic fibers which can be produced by internally cross-linking cellulose fibers with a cross-linking agent. Fibers of this general type are particularly useful in the acquisition/distribution layer described herein and are disclosed, for example, in Bernardin, U.S. Pat. No. 3,224,926, issued Dec. 21, 1965; Steiger, U.S. Pat. No. 3,241,553, issued Mar. 22, 1966; Chung, U.S. Pat. No. 3,440,135, issued Apr. 22, 1969; Steiger, U.S. Pat. No. 3,658,613, issued Apr. 26, 1972; Chatterjee, U.S. Pat. No. 3,932,209, issued Jan. 13, 1976; and Sangenis et al., U.S. Pat. No. 4,035,147, issued Jul. 12, 1977. The disclosure of each of these patents is incorporated herein by reference. Specific types of stiffened, twisted, curled cellulose fiber include cellulose fibers which have been internally cross-linked, for example, with a $C_2$–$C_8$ dialdehyde or a $C_2$–$C_9$ polycarboxylic acid crosslinking agent, while such fibers are in a relatively dehydrated state. Such fibers can be defined in terms of their dry fiber and wet fiber twist counts. Fibers of this type and processes of making the same are described in greater detail in European Patent Publication No. 251,676, published Jan. 7, 1988; and in European Patent Publication No. 252,650, published Jan. 13, 1988 (both filed in the name of The Procter & Gamble Company); U.S. Pat. No. 4,822,453, issued Apr. 18, 1989 to Dean et al.; U.S. Pat. No. 4,888,093, issued Dec. 19, 1989 to Dean et al.; U.S. Pat. No. 4,898,642, issued Feb. 6, 1990 to Moore et al.; and U.S. Pat. No. 5,137,537, issued Aug. 11, 1992 to Herron et al. The disclosure of each of these publications and patents is incorporated herein by reference.

It may be desirable in some applications to include some quantity of hydrophobic fibrous material in the absorbent members, particularly in the acquisition/ distribution layer described herein. Such hydrophobic fibrous materials may include, for example, synthetic fibers comprised of rayon, polyethylene, polypropylene, polyethylene terephthalate, or blends thereof. The use of such hydrophobic fibrous materials, as well as hydrophilic and hydrophilized hydrophobic fibrous materials (synthetic or natural), is described in greater detail in U.S. Pat. No. 5,217,445 issued to Young et al. on Jun. 8, 1993; U.S. patent application Ser. No. 07/625,776, filed in the names of Cook et al. on Dec. 17, 1990, and published as International Publication No. WO/91/11163 on Aug. 8, 1991; and U.S. patent application Ser. No. 07/625,774, filed in the name of Lash on Dec. 17, 1990 and published as International Publication No. WO/91/11162 on Aug. 8, 1991; each being incorporated herein by reference.

Other fibrous materials which may be suitable for inclusion in the absorbent core include capillary channel fibers, such as those described in greater detail in European Patent Publication No. 391,814, filed in the name of the Eastman Kodak Company and published Oct. 10, 1990, which publication is incorporated herein by reference.

In addition to hydrophilic fibrous material, the absorbent member also preferably contains discrete particles of AGM.

AGMs are those materials which, upon contact with liquids such as water and body fluids, imbibe and retain such liquids and thereby form hydrogels. In this manner, liquids discharged into the absorbent core can be acquired and held by the particles, thereby providing enhanced absorbent capacity and/or improved liquid retention performance.

The particles of AGM can be of any desired shape, e.g., spiral or semi-spiral, cubic, rod-like, polyhedral, spherical, etc. Shapes having a large greatest dimension/smallest dimension ratio, such as needles, flakes, and fibers, may also be used herein. Particles also include conglomerates of individual particles. Preferred AGMs for use in the present invention are "nonfibrous" particles such that the length to diameter ratio of the particulate material is about 10 or less, typically about 1 or less.

The AGM can be an inorganic material such as a silica gel or an organic compound such as a cross-linked polymer. However, the AGM will generally comprise a substantially water-insoluble, slightly cross-linked, partially neutralized, hydrogel-forming polymer material. Suitable AGMs include those described in U.S. Pat. RE 32,649, issued to Brandt et al. on Apr. 19, 1988, which is incorporated herein by reference.

The absorbent cores, and especially the ones which are to be used in diapers, adult incontinence products or training pants, will generally employ AGM having an Absorbent Capacity of at least about 10 grams (g), preferably at least about 15 grams, more preferably at least about 20 grams, of Synthetic Urine per gram of AGM. The selection of a particular AGM for use in the absorbent core or a layer thereof can be made to tailor the absorption properties of the absorbent core. For example, the use of AGM having a relatively high Absorbent Capacity in the storage core and a lower Absorbent Capacity in the acquisition/distribution layer is described in U.S. patent application Ser. No. 08/042,950, filed by Payne et al. on Apr. 5, 1993, which is incorporated herein by reference. Absorbent Capacity and a method of determining the same is described in detail in the above referenced U.S. Pat. No. 5,217,445 issued to Young, et al. on Jun. 8, 1993 as "Superabsorbent Material Absorbent Capacity Test Method."

While the AGM particles may have a particle size varying over a wide range, they will typically have an average particle size of from about 50 microns to about 1000 microns. It may sometimes be desirable to use AGMs having a relatively large particle size and other particle size characteristics, since improved absorbent capacity, acquisition, and distribution within the absorbent core may be realized by incorporating such particles. For example, the use of such particulate AGMs is described in detail in the above referenced U.S. patent application Ser. No. 08/042,950 (Payne et al.). AGM particles having relatively large particle size ranges include interparticle cross-linked aggregates such as those described in U.S. Pat. No. 5,149,334, issued Sep. 22, 1992 to Lahrman et al., which is incorporated herein by reference. Relatively large particle size AGMs can also be prepared by agglomeration of smaller particles to produce larger agglomerates. Agglomeration techniques are well known in the art and may involve the use of moisture addition to, or the use of a binder or other type of agglomerating medium with smaller AGM particles.

As noted, the particles of AGM can be in fibrous form. Fibrous AGMs have been previously disclosed in the art, for example, those fibrous AGMs described in *Textile Science and Technology,* Volume 7, Pronoy K. Chatterjee, editor, Elsevier Science Publishers B.V. (The Netherlands), 1985, in Chapters VII and VIII (collectively pages 217–280); "Radiation Grafting of Acrylic and Methacrylic Acid to Cellulose Fibers to Impart High Water Sorbency," A. H. Zahran, et al., J. of App. Polymer Science, Vol. 25, 535–542 (1980); U.S. Pat. No. 3,838,077, Hoftiezer, et al., issued Sep. 24, 1974; U.S. Pat. No. 4,036,588, Williams, et al., issued Jul. 19, 1977; and U.S. Pat. No. 4,986,882, issued Jan. 22, 1991 to Mackey, et al. Each of these references is incorporated herein by reference.

The relative amount of hydrophilic fibrous material and AGM particles used in the absorbent member can vary over a wide range. In order to minimize the thickness of the absorbent article, it may be desired to maximize the concentration of AGM in certain absorbent members, particularly an absorbent member to be used for fluid storage such as the storage layer described herein. Thus, the absorbent member may contain from about 2% to about 90%, typically from about 30% to about 85%, more typically about 30% to about 70%, most typically from about 40% to about 70%, by weight of the absorbent member, of AGM. These relative weight percentages can also be expressed in terms of a fiber:AGM weight ratio, e.g., an AGM weight percentage of from about 2 to about 90 corresponds to a fiber:AGM weight ratio of from about 98:2 to about 10:90, and the like. In addition, the particles of AGM may be dispersed in various weight ratios throughout different regions and thicknesses of the absorbent member.

The absorbent member embodiments comprising a fibrous carrier means and particulate AGM can be formed by methods such as are known in the art, including air-laying a substantially dry mixture of fibers and AGM particles and, if desired or necessary, densifying the resulting web as described in the hereinbefore referenced U.S. Pat. No. 4,610,678 issued to Weisman et al. on Sep. 9, 1986; and laminating the AGM between two or more webs of fibrous material, such as exemplified in U.S. Pat. No. 4,578,068, Kramer et al., issued Mar. 25, 1986, incorporated herein by reference.

Where the AGM is in fibrous form, the fibrous AGM can be combined with other fibrous carrier means according to conventional airlaid or wetlaid web-forming processes, or can be formed into nonwoven sheets, which may consist essentially of fibrous AGM with substantially zero percent carrier means, or which may include carrier means. Nonwoven sheets made from fibrous AGM such as non-acrylate AGM microfibers are available from Arco Chemical Co. (Newtown Square, Pa., U.S.A.), under the tradename FIBERSORB™, and from Japan Exian Co., Ltd. (Osaka, Japan) which markets AGM fibers comprising a polyacrylonitrile core with a polyacrylic acid/polyammonium acrylate skin under the tradename LANSEAL™.

In an alternative embodiment of the present invention, the absorbent member comprises an absorbent foam. Absorbent foams useful in the present invention include the hydrophilic, open-celled foams disclosed in U.S. patent application Ser. No. 07/743,839, filed on Aug. 12, 1991 in the names of DesMarais et al., and published as International Publication No. 93/04092; and U.S. patent application Ser. No. 08/989,270, filed on Dec. 11, 1992 in the names of Dyer, et al.; and the superabsorbent foams described in U.S. patent application Ser. Nos. 08/038,580 and 08/037,803 both filed on Mar. 26, 1993 in the names of Phan et al. Each of the foregoing Patent Applications and the International Publication are incorporated herein by reference.

In another embodiment of the present invention, the absorbent member comprises a sheet material comprised of AGM. Suitable sheet materials include absorbent polymeric macrostructures that are porous and which comprise an interparticle cross-linked aggregate such as described in U.S. Pat. Nos. 5,102,597 and 5,124,188, both issued to Roe et al. on Apr. 7, 1992 and Jun. 23, 1992, respectively; each incorporated herein by reference. Other suitable sheet materials comprising interparticle cross-linked aggregates are described in U.S. patent application Ser. No. 07/684,712, filed on Apr. 12, 1991 in the names of Kolodesh et al.; and U.S. patent application Ser. No. 07/955,635, filed on Oct. 10, 1992 in the names of Rezai et al., each being incorporated herein by reference.

C. (1) A Preferred Absorbent Core Comprising an Acquisition/Distribution Layer and a Fluid Storage Layer In a preferred embodiment as is shown in FIG. 2, the absorbent core 28 has a fluid acquisition/distribution layer and a fluid storage layer (hereinafter alternatively referred to as acquisition/distribution layer and storage layer, respectively). As shown in FIGS. 2 and 3, the acquisition/distribution layer is typically positioned relative to the storage layer such that the absorbent core comprises an upper acquisition/distribution layer and a lower storage layer. For purposes of this invention, the term "upper" refers to the layer of the absorbent core which is nearest to and faces the absorbent article topsheet; conversely, the term "lower" refers to the layer of the absorbent core which is nearest to and faces the absorbent article backsheet (similarly, "upper surface" and "lower surface" refer to the surface of a layer which is nearest to and faces the absorbent article topsheet or backsheet, respectively). An upper fluid acquisition/distribution layer 150 and a lower fluid storage layer 190 are shown in FIGS. 2 and 3. For purposes of the present invention, the upper acquisition/distribution layer and the lower storage layer refer merely to the upper and lower zones of the absorbent core and are not necessarily limited to single layers or sheets of material. As used herein, the term "layer" includes the terms "layers" and "layered." Thus, both the fluid acquisition/distribution layer and the fluid storage layer may actually comprise laminates or combinations of several sheets or webs of the requisite type of materials as hereinafter described.

Absorbent cores comprising an upper acquisition/distribution layer and a lower storage layer suitable for use herein are described in the above referenced and incorporated U.S. Pat. Nos. 4,673,402 (Weisman et al.) and 5,217,445 (Young et al.); International Publication Nos. WO/91/11162 (Lash) and WO/91/11163 (Cook et al.); and U.S. patent application Ser. No. 08/042,950 (Payne et al.).

The fluid acquisition/distribution layer serves to quickly collect and temporarily hold discharged body fluid. A portion of discharged fluid may, depending upon the wearer's position, permeate the acquisition/distribution layer and be absorbed by the storage layer in the area proximate to the discharge. However, since fluid is typically discharged in gushes, the is storage layer in such area may not absorb the fluid as quickly as it is discharged. Therefore, the acquisition/distribution layer hereof also facilitates transport of the fluid from the point of initial fluid contact to other parts of the acquisition/distribution layer.

The acquisition/distribution layer comprises hydrophilic fibrous material as described herein, and is preferably a web comprising chemically stiffened cellulosic fibers such as previously described. The preferred acquisition/distribution layer comprises from about 50% to 100% of these fibers and from 0% to about 50% of a binding means. Exemplary webs comprising chemically stiffened cellulosic fibers are described in detail in the above referenced and incorporated International Publication No. WO/91/11162 and WO 91/11163 and in U.S. Pat. Nos. 5,217,445 and 5,137,537.

The stiffened cellulosic fibers can be provided in web form by various techniques, including airlaying and wetlaying.

The fluid acquisition/distribution layer will generally have an average dry density of less than about 0.30 g/cm$^3$, measured prior to use, and are average density upon wetting to saturation with Synthetic Urine (1.0% NaCl aqueous solution, prepared with distilled water), on a dry weight basis, of less than about 0.20 g/cm$^3$, preferably less than about 0.15 g/cm$^3$. Preferably, the average dry density and density upon wetting to saturation are between about 0.02 g/cm$^3$ and 0.20 g/cm$^3$, more preferably between about 0.02 g/cm$^3$ and about 0.15 g/cm$^3$. The average dry basis weight of the acquisition/distribution layer will typically range from about 0.001 to about 0.10 g/cm$^2$, preferably from about 0.01 to about 0.08 g/cm$^2$, more preferably from about 0.015 to about 0.04 g/cm$^2$. Density and basis weight can be substantially uniform although nonuniform density and/or basis weight, and density and/or basis weight gradients, are meant to be encompassed herein. Thus, the acquisition/distribution layer can contain regions of relatively higher or relatively lower density and basis weight preferably not exceeding the foregoing ranges. Densities and basis weights can be determined as described in the above referenced International Publication No. WO/91/11163. Density and basis weight values include the weight of any AGM that may be present.

The fluid distribution function of the acquisition/distribution layer is of particular importance in order to more fully utilize the capacity of the storage layer. The presence of substantial amounts of AGM in the acquisition/distribution layer which swell upon contact with fluids is believed to adversely affect this function of the acquisition/distribution layer. Therefore, the fluid acquisition/distribution layer preferably contains no more than about 6.0% of AGM. More preferably, the acquisition/distribution layer will be substantially free of AGM, i.e., less than about 2.0%, preferably less than about 1.0%, more preferably zero or essentially zero percent AGM. As used herein, "essentially zero" percent AGM means low amounts (less than about 0.5%) of AGM present in the acquisition/distribution layer incidental to the contact or close proximity of the AGM-containing storage layer with the acquisition/distribution layer.

The fluid storage layer of the preferred absorbent core preferably comprises hydrophilic fiber and AGM, e.g., the fibers and AGMs previously described. The principal function of the fluid storage layer is to absorb discharged body fluid from the acquisition/distribution layer and retain such fluid under the pressures encountered as a result of the wearer's movements. Thus, the storage layer is typically subjacent to (i.e., is a lower storage layer) and in fluid communication with the acquisition/distribution layer. Ideally the fluid storage layer will drain the acquisition/distribution layer of much of its acquired fluid load. Fluids such as body fluids which are discharged into the acquisition/distribution layer and transported to the storage layer can be acquired and held by the AGM, thereby providing the articles herein with enhanced absorbent capacity and/or improved fluid retention performance.

The AGM in the preferred storage layer will typically be in the form of discrete particles distributed within a web of fibrous material as carrier means. Suitable particulate and fibers include those described above. Preferred fibrous carrier means are cellulose fibers, in the form of fluff (airfelt), such as is conventionally utilized in absorbent cores.

The relative amount of AGM and fibrous carrier means may be as previously described in reference to the relative amount of hydrophilic fibrous material and AGM particles for use in the absorbent members.

The AGM can be uniformly distributed in the storage layer. Alternatively, there may be regions or zones of the storage layer which have higher concentrations of AGM than do other regions or zones of the layer (i.e., a gradient). For example, more AGM may be present in regions of relatively high fluid handling requirements (e.g., near the region of fluid discharge) and less AGM at lower demand regions.

The average dry density of the fluid storage layer comprising hydrophilic fibrous carrier means will generally be in the range of from about 0.06 to about 0.5 g/cm$^3$, preferably within the range of from about 0.10 to about 0.4 g/cm$^3$, more preferably from about 0.15 to about 0.3 g/cm$^3$, most preferably from about 0.15 to about 0.25 g/cm$^3$. Typically the basis weight of the fluid storage layer can range from about 0.02 to 0.12 g/cm$^2$, preferably from about 0.04 to 0.08 g/cm$^2$, most preferably from about 0.05 to 0.07 g/cm$^2$. As with the acquisition/distribution layer, density and basis weight need not be uniform throughout the storage layer. The storage layer can contain regions of relatively higher and relatively lower density and basis weight. Basis weight and density values are determined in the same manner as for the acquisition/distribution layer.

The storage layer embodiments comprising the fibrous carrier means can be formed by methods such as are known in the art, including air-laying a mixture of the AGM and fibers and optionally densifying the resulting web as described in the hereinbefore referenced U.S. Pat. No. 4,610,678; and laminating the AGM between two or more webs of fibrous material, such as exemplified in the above referenced U.S. Pat. No. 4,578,068.

The storage layer may (alternatively or additionally) comprise AGM in fibrous form as previously generally described in reference to the absorbent members.

The storage layer can alternatively comprise a single sheet of essentially 100% AGM, for example, the polymeric macrostructures comprising interparticle cross-linked aggregates described in the abovereferenced and incorporated U.S. Pat. Nos. 5,102,597 and 5,124,188; and U.S. patent application Ser. Nos. 07/684,712 and 07/955,635. The storage layer can also comprise a single sheet of absorbent foam such as those described in the above referenced and incorporated U.S. patent application Ser. Nos. 07/743,839; 08/989,270; 08/038,580; and 08/037,803.

The storage layer and acquisition/distribution layer of the absorbent core can be of any desired shape in the unfolded configuration consistent with comfortable fit and/or the sizing limitations discussed herein, including, for example, circular, rectangular, trapezoidal, oblong, hourglass-shaped, dog-bone-shaped, half dog bone shaped, oval or irregularly shaped. The acquisition/distribution layer can be of similar shape or differing shape than the storage layer. The acquisition/distribution layer and the storage layer of the core are preferably elongated, i.e., they are of unequal length and width in the unfolded, flat configuration. The storage layer need not be physically separated from the acquisition/distribution layer and can simply be, for example, a zone of AGM concentration in a continuous web of stiffened cellulose fiber material. More preferably, however, the storage layer of the absorbent core will comprise a separate web which can be used as an insert placed underneath the acquisition/distribution layer, such as shown in FIGS. 2 and 3.

The acquisition/distribution layer of the absorbent core can have a surface area (in an unfolded configuration) which is less than, equal to, or greater than that of the storage layer. In the present invention, the acquisition/distribution layer preferably has a smaller surface area than that of the storage layer and, in fact, can have a surface area that is substantially smaller than that of the fluid storage layer. Generally, the surface area of the acquisition/distribution layer will range from about 25% to about 100%, preferably from about 30% to about 95%, more preferably less than about 90%, most preferably less than about 85%, of the surface area of the storage layer. In addition, the acquisition/distribution layer preferably will not extend beyond the edge of the storage layer at any outer boundary.

In accordance with the present invention, the acquisition/distribution layer of the absorbent core should be placed in a specific positional relationship with respect to the topsheet and the storage layer of the absorbent article. More particularly, the acquisition/distribution layer of the absorbent core must be positioned so that it is effectively located to acquire discharged body fluid and transport said fluid to other regions of the absorbent core. Thus, the acquisition/distribution layer should encompass the vicinity of the point of discharge of body fluids. These areas would include the crotch area and, preferably for males, also the region where urination discharges occur in the front of the diaper. For a diaper, the front of the absorbent articles herein means the portion of the absorbent article which is intended to be placed on the front of the wearer. Additionally, for males, it is desirable for the acquisition/distribution layer to extend to near the front waist area of the wearer to effectively acquire the relatively high fluid load that occurs in the front of the male wearer, and to compensate for directional variations of the discharges. The corresponding absorbent article regions will vary depending upon the design and fit of the absorbent article. FIG. 2 exemplifies one embodiment wherein the acquisition/distribution layer 150 is suitably positioned to receive both bowel and urine discharges for both males and females.

For disposable baby diaper executions, the acquisition/distribution layer of the absorbent core is preferably positioned relative to the elongated topsheet and/or the storage layer such that the acquisition/distribution layer is sufficiently elongated to extend to areas corresponding at least to about 50%, preferably 75%, of the length of the storage layer. The acquisition/distribution layer preferably has a width sufficient to acquire gushes of body fluids without direct discharge of fluid onto the storage layer. Generally, for diapers, such as shown in FIG. 2, the width will be at least about 5 cm, preferably at least about 6 cm.

For purposes of the present invention, sections of the absorbent article can be defined by reference to top surface areas of the unfolded absorbent article found in front of a given point on the line which defines the length of the absorbent article (e.g., along the longitudinal centerline 67).

For purposes of determining such acquisition/distribution layer positioning, the length of the absorbent article will be taken as the normal longest longitudinal dimension of the elongated article backsheet. This normal longest dimension of the elongated backsheet can be defined with respect to the article as it is applied to the wearer. When worn, the opposing ends of the backsheet are fastened together so that these joined ends form a circle around the wearer's waist. The normal length of the backsheet will thus be the length of the line running through the backsheet from: (a) the point on the edge of the backsheet at the middle of the wearer's back waist, through the crotch, to (b) the point on the opposite edge of the backsheet at the middle of the wearer's front waist. The length of the topsheet will generally correspond substantially to that of the backsheet.

In the usual instance wherein the storage layer of the absorbent core generally defines the shape of the absorbent article, the normal length of the elongated article topsheet will be approached by the longest longitudinal dimension of the storage layer of the core. However, in some applications (e.g., adult incontinence articles) wherein bulk reduction or minimum cost are important, the storage layer would not take on the general shape of the diaper or incontinence structure. Rather the storage layer would be generally located to cover only the genital region of the wearer and a reasonable area proximate to the genital area. In this instance both the fluid acquisition/distribution layer and the storage layer would be located toward the front of the article as defined by the topsheet such that the acquisition/distribution and storage layers would typically be found in the front two-thirds of the article.

In yet another embodiment, a fluid pervious sheet (e.g., a paper tissue sheet) is positioned between the acquisition/distribution layer and the storage layer to increase integrity of the acquisition/distribution layer during processing and/or use. Such a fluid impervious sheet is shown in FIGS. 2 and 3 as tissue layer 170. The fluid pervious sheet can envelope all or part of the acquisition/distribution layer (e.g., as shown in FIGS. 2 and 3), or simply be positioned as described above without necessarily enveloping any of the edges of the acquisition/distribution layer. Additionally or alternatively, the storage layer can be enveloped with a fluid pervious sheet to obviate user concerns with loose AGM which may be present in the storage layer.

D. The Primary Core Integrity Layer

The diaper 20 comprises at least one absorbent core integrity layer, the primary core integrity layer (additional, optional absorbent core integrity layers are referred to herein as secondary core integrity layer(s)). The primary core integrity layer can be positioned adjacent the body facing surface or the garment facing surface of the absorbent core, i.e., between a chassis component (i.e., the topsheet or backsheet) and the absorbent core. The primary core integrity layer can alternatively be positioned within the absorbent core. For example, the primary core integrity layer can be positioned within a monolayer absorbent core, or within a layer or between layers of a multilayer absorbent core. As shown in FIGS. 2–3, the primary core integrity layer 120 is positioned adjacent the garment facing surface of the absorbent core 28, between the backsheet 26 and the absorbent core 28.

The primary core integrity layer can be of any desired size and shape as long as the dimensions are sufficient to improve the integrity of the absorbent core or layer thereof. This layer can be a unitary structure or can comprise a multiplicity of patches or strips of suitable material as described herein. The body facing surface and the garment facing surface of the primary core integrity layer have substantially the same surface area. This surface area can be the same as, greater than, or less than that of the absorbent core or one or more layers thereof. In other words, one or more of the edges of the primary core integrity layer may be registered with, positioned inside of, or extend beyond one or more of the edges of one or more layers of the absorbent core. As shown in FIG. 2, the end edges and the side edges of the primary core integrity layer extend beyond (i.e., outside) of the end edges and at least a substantial longitudinal portion of the side edges of these layers.

Thus, in one embodiment of the present invention, the surface area dimensions of the primary core integrity layer are less than those of the absorbent core or, in a multilayer absorbent core, one or more layers thereof. Accordingly, one or more of the edges of the absorbent core or layer(s) thereof may extend beyond the periphery of the primary core integrity layer. This embodiment may be preferred for industrial hygiene and/or economic reasons provided that sufficient absorbent core integrity is realized for a particular application. In a preferred embodiment wherein the absorbent core comprises an acquisition/distribution layer and a storage layer, the primary core integrity layer according to this aspect of the invention is positioned between the acquisition/distribution layer and the storage layer, the side edges of the acquisition/distribution layer and of the storage layer extending beyond the side edges of the primary core integrity layer. A tissue layer can be placed between the primary core integrity layer and the storage layer such that the side edges of the tissue layer also extend beyond those of the primary core integrity layer. In these embodiments, the end edges of the primary core integrity layer may alternatively be registered with, extend inside, or extend outside of the end edges of the acquisition/distribution layer, storage layer, and/or optional tissue layer. Preferably, the end edges of the primary core integrity layer are registered with or inside of the end edges of these absorbent layers.

For reasons of enhanced absorbent core integrity and absorbent article absorption performance, it will generally be preferred that the primary core integrity layer has surface area dimensions such that it extends beyond at least a portion of at least one edge (side or end) of the absorbent core or, in a multilayer absorbent core, one or more, preferably each, layer thereof. Thus, the primary core integrity layer envelopes at least a portion of at least one edge (side or end) of the absorbent core, or one or more layers thereof, between the primary core integrity layer and a chassis component or another absorbent core layer. The primary core integrity layer preferably extends beyond at least a portion of one or more of the edges of the absorbent core or layer(s) thereof such that the primary core integrity layer can be directly joined to a chassis component. Without intending to be bound by theory, it is believed that direct joinder in this fashion provides relatively cohesive bonding that enhances absorbent core integrity. In a multilayer core, it Will often be desirable for absorption performance reasons to envelope at least one edge of each of the layers of the absorbent core in this manner. It should be understood, however, that sufficient improvements in absorbent core integrity for a given application may be obtained by using a configuration in which the primary core integrity layer envelopes an edge of only one or some of the absorbent layers of the absorbent core 28.

As shown in FIG. 2, the primary core integrity layer 120 envelopes at least a portion of the side edges 152, 172, and 192 to enable direct joinder of the primary core integrity layer, the topsheet, and the backsheet. The primary core integrity layer envelopes at least the portion of the side edges 152, 172, and 192 positioned in the absorbent core crotch region 57a. As shown in FIG. 2, the primary core integrity layer 120 envelopes the side edges 152 and 172, and side edges 192 exclusive of the side edge portions 192a lying in the absorbent core ears 102.

The primary core integrity layer provides structural support to the absorbent core (as will be understood by one skilled in the art, this and the following discussion also apply to effects on individual layers of the absorbent core). Without intending to be bound by theory, it is believed that the higher elasticity and/or flexibility of the primary core integrity layer relative to those properties of the fibrous materials of the absorbent core tend to allow the absorbent core to withstand the various forces encountered during manufacture and use of an absorbent article (e.g., flexural and torsional forces). As a result, the absorbent core has a reduced tendency to break, for example, during use or after being subjected to the forces typically used in packaging disposable absorbent articles. Thus, the absorption by the absorbent core is not limited by breakage gaps which may otherwise occur in the absorbent core such that the entire absorbent core tends to be available for fluid absorption.

The primary core integrity layer may additionally serve to hold the absorbent core in a relatively stable position, since the absorbent core may be physically constrained by the primary core integrity layer, e.g., where the primary core integrity layer envelopes an edge of the core and is directly joined to a chassis component. Similarly, the primary core integrity layer may help to maintain the bonds which typically join the absorbent core and chassis component of absorbent articles, for example, the construction adhesive bonds typically joining cellulosic fibers of the absorbent core to a synthetic polymeric chassis.

Without intending to be bound by theory, it is believed that the thermoplastic material from which the primary core integrity layer is made forms a bond to a synthetic polymeric chassis component (whether directly joined to the chassis component by its own adhesive properties or by a construction adhesive) having a greater strength than the adhesive bond between cellulose fibers and the chassis. This is because the former bond tends to be relatively cohesive, as compared to the latter bond. It is believed that the more similar the chemistry of the materials being joined, the greater the bond strength. Further, if the bonds joining the cellulose fibers of the absorbent core and the chassis do fail, these relatively cohesive bonds tend to retain the absorbent core in a relatively stable position. Thus, the absorbent core has a reduced tendency to separate from the chassis component. This positive effect on adhesion tends to be particularly important when the absorbent article is wetted since, when the cellulosic fibers and AGM which are typically incorporated into the absorbent core expand upon wetting, the forces exerted by their expansion tend to cause a loss of adhesion between the fibers, AGM, and chassis.

By effectively constraining the absorbent core, the primary core integrity layer also reduces the tendency of absorbent core layers to slip away and/or separate from one another. This tendency toward slippage and/or separation is further reduced where the primary core integrity layer comprises a tacky, pressure-sensitive material.

Without intending to be limited by theory, it is also believed that the greater the penetration of the thermoplastic material of the primary core integrity layer into a fiber layer of the absorbent core, the greater the mechanical adhesion between the fibers and the primary core integrity layer with a resultant enhancement in absorbent core integrity. These effects tend to be particularly important in regard to enhancing the integrity of an acquisition/distribution layer adjacent a core integrity layer as described herein. As will be understood by the skilled artisan in light of the teachings herein, the thermoplastic materials and/or process conditions may be selected to cause such increased penetration and resultant integrity improvement. For example, the use of a high wet strength adhesive and/or a melt blown or spray process tends to cause such increased penetration with resultant improvements in absorbent core integrity.

It is believed that the above described features of the primary core integrity layer reduce the tendency of the absorbent core or components thereof to slump, break, and/or rope. As a result, the absorbent core is more effectively utilized such that the absorbent article has improved absorption characteristics and reduced leakage.

The primary core integrity layer provides the above improvements without substantially reducing fluid transport into and through the absorbent core or reducing softness or flexibility of the absorbent core, and without requiring a great amount of material.

The primary core integrity layer comprises a continuous, liquid pervious mesh of strands of thermoplastic material.

By "mesh" it is meant that the strands overlap to form apertures. By "continuous" mesh, it is meant that substantially all of the strands are connected to at least one other strand at the point of overlap. Typically, the strands are connected, generally cohesively connected, at each of the points where the individual strands overlap. (As understood in the art, "cohesion" and the like refers to the force that holds adjacent molecules of a single material together. As used herein, "relatively cohesive" bonding is believed to result from the force of attraction between two or more similar materials, e.g., two or more synthetic polymeric materials).

By "liquid pervious mesh," it is meant that the mesh has a sufficient number of apertures of sufficient size per unit area to allow relatively unimpeded fluid transport through the mesh. Thus, the mesh typically has a strand denier and basis weight as described herein. "Strands" is meant to include fibers, threads, filaments, and other forms which have a relatively large longitudinal to cross-sectional dimension.

As formed by the processes described herein, the strands of the primary core integrity layer tend to form a relatively planar structure as positioned in the absorbent article in a flat, unfolded configuration. One skilled in the art will recognize, however, that the thermoplastic material may penetrate into a layer of the absorbent article, particularly an absorbent core layer containing fibers, during the formation of the primary core integrity layer.

Various thermoplastic materials such as are known in the art may be used for making the primary core integrity layer. Suitable thermoplastic, materials include hot-melt adhesives, including elastomeric, pressure-sensitive, and/or high wet strength hot-melt adhesives. A "thermoplastic" material, as that term is used and understood by those skilled in the art, includes any natural or synthetic thermoplastic polymer or polymeric composition. A thermoplastic material is normally a solid or semi-solid material at use temperatures (typically room temperature, i.e., about 20° C. to about 25° C.) which melts or liquefies upon heating to a higher temperature. Upon cooling, the material solidifies or returns to a solid or semi-solid state. As also used in this description, the term "hot-melt adhesive" is a term which is well known in the art, which material has the same characteristics of liquefaction upon heating and, upon cooling, solidification to a solid, semi-solid, or tacky state. Hot-melt adhesives are typically melted or liquefied to cause flow and then solidified upon cooling after contacting an adherence (i.e., substrate), generally under moderate pressure.

The thermoplastic material used to form the primary core integrity layer may advantageously be obtained by recycling excesses of a material that is already in use in other components of the absorbent article, for example, in the backsheet or topsheet.

Examples of thermoplastic materials include polymers of ethylenically unsaturated monomers such as polyethylene, polypropylene, polystyrenes, polyvinyl chloride, polyvinyl acetate, polymethyl methacrylate, polyethyl acrylate, polyacrylonitrile, and the like; copolymers of ethylenically unsaturated monomers such as copolymers of ethylene and propylene, styrene, or polyvinyl acetate; styrene and maleic anhydride, methyl methacrylate, ethyl acrylate, or acrylonitrile; methyl methacrylate and ethylacrylate; and the like;

polymers and copolymers of conjugated dienes such as polybutadiene, polyisoprene, polychloroprene, styrene-butadiene rubber, ethylene-propylene-diene rubber, acrylonitrile-styrene butadiene rubber and the like; saturated and unsaturated polyesters including alkyds and other polyesters; nylons and other polyamides; polyesteramides and polyurethanes; chlorinated polyethers; epoxy polymers; and cellulose esters such as cellulose acetate butyrate, and the like. Blends of thermoplastic materials can also be used, including, but not limited to, physical mixtures and copolymers. Particularly suitable thermoplastic materials include polyethylene, polypropylene, polyesters, ethylene vinyl acetate, and blends thereof.

Hot-melt adhesives are typically based on one or more types of thermoplastic materials, such as those described above. Thus, the hot-melt adhesives used herein may be a thermoplastic material or, preferably, a composition comprising a thermoplastic material. The various hot-melt adhesives known in the art are suitable for use herein.

By "elastomeric," "elastic," etc., it is meant that the material is able to be stretched to at least twice its original length and to retract to approximately its original length when released. Exemplary elastomeric:, hot-melt adhesives include thermoplastic elastomers such as ethylene vinyl acetates, polyurethanes, polyolefin blends of a hard component (generally a crystalline polyolefin such as polypropylene or polyethylene) and a soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers; mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprene-styrene block copolymer with polystyrene; and the elastomeric, hot-melt, pressure-sensitive adhesives described herein. Elastomeric, hot-melt adhesives of these types are described in more detail in U.S. Pat. No. 4,731,066 issued to Korpman on Mar. 15, 1988, which is incorporated herein by reference.

Hot-melt, pressure-sensitive adhesives, as understood by those of ordinary skill in the art, have some degree of surface tack at use temperatures. These tacky materials typically have a viscosity at room temperature (about 20° C. to about 25° C.) which is sufficiently low to permit good surface contact yet high enough to resist separation under stress, typically on the order of $10^4$–$10^6$ centipoise. Due to their surface tack, the pressure-sensitive adhesives used herein tend to increase the coefficient of friction between absorbent article components which may be adjacent to the pressure-sensitive adhesive, for example, the absorbent core layers. In addition, the pressure-sensitive adhesives provide manufacturing flexibility since joinder of the primary core integrity layer to other absorbent article components may then occur via the pressure-sensitive properties of the adhesive after the adhesive has solidified. Various hot-melt, pressure-sensitive adhesives are known in the art and are suitable for use herein.

Hot-melt, pressure-sensitive adhesives that are also elastomeric are disclosed in the above referenced and incorporated U.S. Pat. No. 4,731,066, and include those materials based on thermoplastic block copolymers, polyacrylates, and ethylene vinyl acetate. Suitable elastomeric, hot-melt, pressure-sensitive adhesives include the A-B-A block copolymer based adhesives which are specified as H-2085 and H-2031 by Findley Adhesives, Inc., of Wauwatosa, Wis.

High wet strength, hot-melt adhesives include those that have a relatively slow crystallization rate such that they remain in a liquid state for a relatively long period of time after application or exhibit sufficient cold flow so as to allow physical penetration into and around the components of the s absorbent core, typically the fibers of an absorbent core layer comprising fibers, e.g., cellulosic fibers. Adhesives having a relatively slow crystallization rate tend to flow or spread over an extended period at room temperature (about 21° C.). For example, a bead of such an adhesive having an initial 2" length, 0.5" width, and 0.5" height may flow over a period of at least about 24 hours at 70° F. to form a bead having about a 2.75" length, 1.5" width and 0.12" height. In comparison, adhesives having a relatively fast crystallization rate substantially retain the initial length, width, and height dimensions. Adhesives having relatively slow crystallization rates tend to have a higher wet strength than ordinary hot-melt adhesives and do not dissolve when wet.

The Wet Peel Strength and the Dry Peel Strength of adhesives can be measured by the following Peel Test. In general, a laminate is formed by bonding a strip of film and tissue with the adhesive to be tested. The tensile peel strength of the laminate is then determined after dry or wet aging of the laminate.

The laminates to be tested can be prepared as follows. A single, 0.75 inch (1.9 cm) wide spiral of adhesive is applied to a 1" (2.54 cm) wide, suitably long strip of plain thermoplastic polyethylene film backsheet material (described hereinabove) at an adhesive add-on level of 2 mg/in adhesive. For application of the adhesive, the adhesive temperature is typically at about 300° F. (149° C.) and the air temperature is typically at about 400° F. (204° C.). The adhesive may be applied using any suitable equipment. Suitable equipment for the adhesive application includes an Acumeter LH-1 coater made by Acumeter Laboratories, Inc. of Marlborough, Mass. or an equivalent thereof such as is available from the May Coating Company of St. Paul, Minn.

A 1 inch (2.54 cm) wide, suitably long strip of envelope grade tissue is then positioned on the adhesive layer to form a laminate, such that the long edges of the film strip and the tissue strip overlap.

A suitable tissue has a basis weight of from 19.4–21.3 g/m$^2$, a dry tensile strength in the machine direction (MD) of from 600–1,250 g/in, a dry tensile strength in the cross direction (CD) of from 250–700 g/in, a wet CD tensile strength of from 85–175 g/in, and a MD tensile % elongation at break of from 9–16. The tensile data is generated using a universal constant rate of elongation tensile testing machine such as are known in the art at a crosshead speed of 4"/minute and a gauge length of 4" or as follows. For dry tensile testing, if the tissue roll (from which the tissue samples may be supplied) width is less than 7", a gauge length of 2" is used; if the tissue roll width is less than 5", a gauge length of 1.5" is used. For CD wet tensile testing, if the roll width is less than 10" the tensiles are run with a 1.5" gauge length. Testing is performed in a 73°±2° F., 50±2% Relative Humidity room.

A wet strength tensile cup such as are known in the art, e.g., a 1" wide cup such as a Finch Wet Strength Device from Thwing-Albert Instrument Co. of Philadelphia, Pa. is used for measuring wet tensiles. The tissue sample is symmetrically looped across its width around the horizontal bar of the cup and positioned in the tester such that it is centrally located with respect to the bar and the upper tester clamp. The looped end of the sample is immersed to a depth of at least ¾" in the water which is placed in the cup. The tester is engaged 5 seconds after the immersion at this depth is begun.

The above stated values are the average of 4, 1" wide tissue strips. Samples to be dry tested are 8" long single ply and are conditioned for at least 2 hours at 73°±2° F., 50±2% Relative Humidity. Samples to be wet tested are preferably at least 10" long single ply (two-ply when looped in the wet tensile cup) and are conditioned for 1 hour at 165±–5° F. For CD testing, the strips are cut from a suitable tissue in the CD. Similarly, for MD testing, the strips are cut in the MD.

The polyethylene film—tissue laminate is then nipped at a compression of 2 bar between two rollers (one steel and one rubber). An open time of 0.25 seconds is allowed between the time of adhesive application to the film and nipping. Prior to nipping, 1" wide, 2" long pieces of paper are inserted between the film and tissue strips so as to mask a 2" length of the adhesive at uniform intervals of the laminate. The total bonding area between the pieces of paper is 12 in$^2$. The laminate is then cut into samples having a 1"×6" bonded area and a 1"×1" non-bonded area (i.e., uncoated leader areas).

For determining the Dry Peel Strength, a sample is held at ambient conditions, typically 70°±2° F., about 50±2% relative humidity, for 24 hours. The sample is then tested as described below. For determining the Wet Peel Strength, the sample is additionally soaked in water at a temperature of 70°±2° F. for one hour. The sample is then removed from the water, blotted dry and tested as described below. Testing is performed at ambient conditions (70°±2° F./50±2% relative humidity).

The 180° tensile peel strength of the sample is then determined using a universal constant rate of elongation tensile testing machine in the following manner. Suitable tensile testing equipment includes the Instron Series IX Data Systems Adapter; Instron Model 1122, and equivalents thereof. The tensile tester is calibrated and the machine parameters of the test are set at a sample rate of 4.55 points/sec, a constant crosshead speed of 12 in/min, and a full scale load range of 5 lbs.

The lower jaw of the tensile tester is positioned to within 0.75" of the upper jaw and the displacement scale is set to zero. The uncoated leader areas are placed in the jaws of the tester with the free film end placed in the lower clamp and the free tissue end placed in the opposing, upper clamp and the jaws are closed. The sample is then pulled and the tensile strengths of the sample recorded. The first 5% and the last 5% of the data points are discarded.

The average load between the crosshairs and the load at maximum are reported. The average load between the crosshairs in grams/inch width is the average value of all of the data points collected over the time of the test. The load at maximum in grams/inch width is the maximum amount of force produced at one individual point over the time of the test. A total of 6 samples for each are tested for each adhesive type. The average load at maximum in grams/inch strip width is the Dry Peel Strength or the Wet Peel Strength, as applicable.

A visual observation is made of each sample in order to determine the mode of bond failure. Bond failure is reported as cohesive failure (failure of the adhesive), adhesive failure (failure of the bond between the substrate and adhesive) or substrate destruct (failure of the substrates with little or no delamination of the bond). A relatively subjective composition of each type of failure may be reported, for example, 50% cohesive failure, 40% adhesive failure from the polyethylene film strip, and 10% fiber tear of the tissue strip. Where tissue failure occurs prior to adhesive failure (substrate destruct), the peel strength is reported in terms of a minimum value.

Typical construction adhesives used in diapers have a Dry Peel Strength of at least about 35 g/in (13.8 g/cm) and a Wet Peel Strength of about 2.6 g/in (1 g/cm). The high wet strength adhesives referred to herein preferably have a Wet Peel Strength of at least about 4 g/in (1.6 g/cm), more preferably at least about 6 g/in (2.4 g/cm), and most preferably at least about 8 g/in (3.1 g/cm). The high wet strength adhesives may, for example, have a Dry Peel Strength of at least about 22 g/in (8.7 g/cm) and a Wet Peel Strength of at least about 9 g/in (3.5 g/cm). Suitable high strength adhesives include Findley Adhesive H4071-01 manufactured by the Findley Adhesive Company of Elm Grove, Wis. and H. B. Fuller Adhesive 1262 manufactured by the H. B. Fuller & Company of St. Paul, Minn.

The strands of the primary core integrity layer are overlapping so as to form apertures. Depending on the process used to manufacture the primary core integrity layer, the strands can be relatively long, continuous strands or discrete strands of random length. Moreover, the individual strands can be oriented in various degrees of randomness. In general, the strands are sinuous (wavy) with at least some crosswise linking to form an interconnecting web of the strands. Whatever the form of the strands, they form a continuous mesh that provides sufficient integrity to the absorbent core and yet does not substantially reduce absorption by the absorbent core. In addition, the primary core integrity layer should not significantly reduce the softness or flexibility of the absorbent core.

The properties of the primary core integrity layer and thus of the absorbent core and absorbent article are influenced by the strand orientation, strand denier, primary core integrity layer basis weight, and the type of the thermoplastic material making up the strands.

The strand orientation influences the softness and flexibility of the absorbent article. In general, the softness and/or flexibility increases as the orientation of the overlapping strands becomes more random. Therefore, the individual strands are preferably oriented in substantially random position to other strands of the mesh, i.e., the individual strands are in relatively random geometrical position. Thus, the strands may be oriented so as to form a reticulated network of the strands wherein the angles formed by the points of overlap of the individual strands are substantially nonuniform throughout the mesh. Random orientation of the strands tends to enable flexing of the primary core integrity layer in multiple directions relative to the relatively planar structure of the layer as configured in the absorbent article in a flat, unfolded configuration, without breakage of the layer. For example, the primary core integrity layer may be flexed along a tranverse line to form an angle of at least about 90° relative to the forementioned relatively planar structure. In contrast, core integrity layers having strands laid in a relatively uniform geometric fashion, for example, so as to form a 90° grid, tend to be relatively inflexible. Such core integrity layers typically cannot be flexed along a transverse line to form an angle of more than about 45°, without breakage occurring.

Strand denier influences absorbent core softness and flexibility. For a given adhesive, orientation, and basis weight, the softness and flexibility increases with decreasing strand denier. A suitable balance of absorbent core softness, flexibility and integrity is typically achieved with a strand denier of at least about 60 microns, preferably from about 80 microns to about 200 microns, more preferably about 90 to about 200 microns, most preferably about 100 to about 200 microns.

The basis weight of the primary core integrity layer influences absorption by the absorbent core. The basis weight of the primary core integrity layer also influences the softness and flexibility of the absorbent core. Typically, a suitable balance of absorbent core absorption, softness, flexibility, and integrity is achieved when the basis weight of the primary core integrity layer is from about 2 to about 8 grams/square meter ($g/m^2$), preferably about 3 to about 7 $g/m^2$, more preferably about 4 to about 6 $g/m^2$, most preferably about 5 $g/m^2$.

The type of thermoplastic material forming the strands of the primary core integrity layer influences the flexibility of the absorbent core. For a given strand denier, strand orientation, and primary core integrity layer basis weight, an elastomeric thermoplastic material tends to provide greater flexibility than non-elastomeric materials. Therefore, elastomeric materials are generally preferred for enhancing the flexibility of the absorbent article.

The strand orientation, strand denier, and primary core integrity layer basis weight may be substantially uniform or variable throughout the primary core integrity layer. Thus, the primary core integrity layer can be designed and positioned in the absorbent article to tailor the integrity and absorption properties of the absorbent core and absorbent article. For example, the primary core integrity layer can have a relatively low basis weight region of relatively fine denier, random, discrete strands positioned in the fluid acquisition region of the absorbent article, and a relatively high basis weight region of relatively large denier, continuous strands positioned adjacent the fluid acquisition region (e.g., in the areas corresponding to the end and/or side edges of the absorbent core). The relatively low basis weight region tends to improve the integrity of the core while reducing the risk of interfering with absorption by the core. The relatively high basis weight region is believed to provide strength to the peripheral regions of the absorbent core and article.

The primary core integrity layer can be formed using a meltblown fiber process or spray process. Such processes and equipment therefor are generally known in the art. In these processes, the thermoplastic material is heated to and held at a temperature sufficient to allow processing, typically at least until the material is in a liquid or molten state (melt/liquefaction temperature). (In general, the selection of any given temperature in the process is limited by the degradation temperature of the particular thermoplastic material being processed.) The molten/liquefied material is extruded under pressure (at an extrusion temperature and pressure) through orifices. Upon extrusion, the molten/liquid material is subjected to air flowing under pressure (the air being at a suitable air temperature and air pressure) that stretches and/or shreds the material to thereby fiberize the material (strands are formed). The extrusion temperature and air temperature are selected in order to facilitate strand formation. During and/or after strand formation, the thermoplastic material cools to form stabilized strands of the thermoplastic material. The apparatus is configured such that the strands are laid onto a desired substrate.

In the present invention, the process parameters are selected to provide a mesh having the desired strand orientation, denier, and basis weight. These parameters include the number and size of the orifices, melt/liquefaction temperature, extrusion temperature, extrusion pressure, air pressure, air temperature, and the orifice to substrate distance.

The size of the orifice influences the strand denier and basis weight. As the orifice size increases, the denier and basis weight tend to increase. The basis weight also tends to increase with the number of orifices. The size of the orifice(s) is typically from about 0.010"–0.040" in diameter. In general, the number of orifices is from about 8–30/inch, typically about 10/inch. For example, the J and M Laboratories meltblown equipment described herein may have about 10 orifices having a 0.020" diameter/inch.

The melt/liquefaction temperature and particularly the extrusion temperature influence the strand denier and orientation. In general, as these temperatures increase, the viscosity of the thermoplastic material being processed decreases such that the strand denier decreases and the strand orientation becomes more random. The high wet strength adhesives described herein tend to have a lower viscosity at a given temperature than other adhesives, e.g., the elastomeric hot melt adhesives described herein. Thus, for a given set of process temperatures and pressures, the high wet strength adhesives tend to form strands having a finer denier and that are distributed more randomly on the substrate, relative to the other adhesives. Accordingly, in general lower process temperatures and/or pressures are needed to provide a high wet strength mesh having a morphology similar to that formed by other adhesives which are processed at higher temperatures and/or pressures. Typically the process variables, including the melt/liquefaction temperature and the extrusion temperature, are set for a particular adhesive so as to provide a mesh having a basis weight and strand denier as previously described.

The melt/liquefaction temperature is typically from about 121° C. (250° F.) to about 204° C. (400° F.), preferably about 149° C. (300° F.) to about 190° C. (375° F.). For high wet strength adhesives such as Findley H4071-01 and Fuller 1262, the adhesives are typically held at a temperature of from about 121° C. (250° F.) to about 190° C. (375° F.), preferably about 135° C. (275° F.) to about 163° C. (325° F.), more preferably about 152° C. (305° F.). The adhesives designated H-2031 and H-2085 are typically held at a temperature of from about 135° C. (275° F.) to about 204° C. (400° F.), preferably about 149° C. (300° F.) to about 177° C. (350° F.), more preferably about 165° C. (330° F.).

The extrusion temperature is typically at or above the melt/liquefaction temperature, preferably above the latter temperature in order to facilitate strand formation. For high wet strength adhesives such as Findley H4071-01 and Fuller 1262, the extrusion temperature is typically from about 135° C. (275° F.) to about 190° C. (375° F.), preferably about 149° C. (300° F.) to about 177° C. (350° F.), more preferably about 168° C. (335° F.). For other adhesives, such as H-2031 and H-2085, the extrusion temperature is typically from about 149° C. (300° F.) to about 204° C. (400° F.), preferably about 163° C. (325° F.) to about 190° C. (375° F.), more preferably about 182° C. (360° F.).

The extrusion pressure influences the velocity of the extruded thermoplastic material (in transit from the orifice to the substrate) and, combined with the hot air pressure, may affect the randomness of the strand orientation and the penetration of the thermoplastic material into the substrate, as will be readily understood by the skilled artisan. The extrusion pressure is typically from about 250 to about 850 psi, preferably from about 500 to about 600 psi.

The air pressure influences both strand orientation and denier. The particular air pressure can be selected for a given adhesive and set of process temperatures to obtain a desired strand denier and orientation. For a given material and set of process temperatures (particularly extrusion and air temperatures), as the air pressure increases the strands tend to form in a more random orientation and with a finer denier. The air pressure is at least high enough to form strands of molten/liquefied thermoplastic material which overlap and thus are capable of interconnecting while the thermoplastic material is in a sufficiently molten/liquid state, as described below. Typically, the air pressure will be from about 1 psi to about 15 psi. For a high wet strength adhesive and process temperatures as described above in reference to these adhesives, the air pressure is preferably from about 1 to about 8 psi, more preferably from about 1 to about 6 psi, most preferably from about 1 to about 4 psi. Where the strands of the primary core integrity layer comprise a thermoplastic material other than the high wet strength adhesives described herein, for example, a non-high wet strength, elastomeric and/or pressure-sensitive hot-melt adhesive, the air pressure is preferably from about 3 psi to about 15 psi, more preferably about 3 to about 10 psi, even more preferably about 3 to about 8 psi, most preferably about from about 3 to about 6 psi.

The air temperature influences the strand denier and the interconnection of the strands of the mesh. The strand denier tends to decrease, and the interconnection tends to increase with an increase in the air temperature. The air temperature will generally be selected so as to maintain the extruded thermoplastic material in the molten/liquefied state. Thus, the air temperature will usually be greater than or equal to the extrusion temperature in order to offset any cooling effects which might, otherwise occur. Preferably, the air temperature is sufficient to ensure the interconnection of the individual strands of thermoplastic material on the substrate (although the extruded material need not be in the same melt/liquefaction state as when first extruded, it is preferably sufficiently molten/liquefied to enable interconnection of the strands). For the high welt strength adhesives described herein, the air temperature is typically from about 177° C. (350° F.) to about 210° C. (410° F.), preferably from about 188° C.: (370° F.) to about 199° C. (390° F.), more preferably about 249° C. (480° F.). For other thermoplastic materials such as the adhesives designated H-2031 and H-2085, the air temperature is typically from about 204° C. (400° F.) to about 238° C. (460° F.), preferably from about 215° C. (420° F.) to about 227° C., (440° F.), more preferably about 221° C. (430° F.). Upon cooling to a temperature sufficient to resolidify the thermoplastic material, the resultant mesh of interconnected strands is stabilized.

The orifice to substrate distance influences the strand denier and orientation. As the distance increases, the denier tends to decrease with the orientation becoming more random. The distance typically ranges from about 0.75 inches to about 3.50 inches and is more typically from about 1.25 inches to about 1.50 inches.

In general, any factor that increases the adhesive extrusion rate tends to increase the basis weight of the resultant mesh. The extrusion rate, and thus the basis weight, increases with the melt/liquefaction and extrusion temperature, the extrusion pressure, and the size of the orifice.

Suitable equipment for manufacturing the primary core integrity layer includes the meltblown glue guns available from J and M Laboratories of Dawsonville, Ga. The J and M Laboratories meltblown glue gun apparatus extrudes the thermoplastic material through multiple nozzles and in relative linear position of a known diameter, for example, a standard nozzle configuration is ten 0.020 inch diameter nozzles per inch. Another suitable system for making the primary core integrity layer is the "Control Coat System," available from Nordson Corporation of Duluth, Ga. The Nordson apparatus extrudes the thermoplastic material through a slot of known thickness. The slot design uses a shim plate to determine the slot dimensions, the shim thickness influencing the resultant strand denier. In both the J and M Laboratories and the Nordson apparatus, the extruded material is impinged by hot air at a set pressure from two parallel slots of known thickness on either side of the nozzle or slot, respectively, to thereby fiberize the material.

The particular equipment used to manufacture the primary core integrity layer is typically selected according to whether it is desired to envelope an edge of the absorbent core or layer(s) thereof. For example, if it is desired to envelope the side edges of the absorbent core, equipment is preferably selected which will provide, in one step, a width of mesh of thermoplastic material which is sufficient to envelope the side edges of the absorbent core. In contrast, the equipment may be selected to provide a mesh width which is smaller than the width of the absorbent core component. J and M Laboratories' 2 module, 3.0" width meltblown glue gun designated AMBI-3.0-2 and 4 module, 6" width meltblown glue gun designated AMBI-6.0-4 are suitable for use herein.

The primary core integrity layer is preferably formed on-line in a continuous or intermittent process during manufacture of the absorbent article, with another diaper component serving as the substrate upon which the primary core integrity layer is formed. An on-line process tends to enable adhesion of the primary core integrity layer to the diaper component via the hot-melt properties of the thermoplastic material making up the primary core integrity layer. Alternatively, the primary core integrity layer may be preformed in an intermediate process for later incorporation into the absorbent article.

The primary core integrity layer is joined to the adjacent absorbent article components (i.e., the absorbent core, layer thereof, or one or more chassis components). The layer can be joined to a component by a construction adhesive, by the melt or pressure-sensitive properties of the thermoplastic material of the primary core integrity layer, or by any combination thereof.

In a preferred embodiment, the primary core integrity layer is joined, more preferably directly joined, to a chassis component. The primary core integrity layer is preferably joined to the chassis component by or with the aid of a construction adhesive. It is believed that the use of a construction adhesive tends to form a higher strength bond than that formed solely via the melt or pressure-sensitive properties of the primary core integrity layer material such that the absorbent core integrity is enhanced. It is further believed that this bond strength will be higher where the construction adhesive material is the same as the material used to form the primary core integrity layer; for this reason this embodiment is more preferred. However, for economic reasons, it may not be desirable to use the same types of materials for the construction adhesive and the primary core integrity layer.

Suitable construction adhesives include any of the adhesive materials such as are known in the art of bonding absorbent cores to chassis components, including those described herein in reference to joining the backsheet and the primary core integrity layer (alternatively the absorbent core). The construction adhesive can comprise any of the hot-melt adhesives described in reference to the thermoplastic materials for forming the primary core integrity layer.

The construction adhesive can be applied to a given substrate (e.g., the primary core integrity layer, an absorbent core component, or a chassis component) by any suitable method that does not undesirably reduce the fluid handling properties of the article, for example, by the methods as described herein in reference to joinder of the backsheet and the primary core integrity layer.

Joinder of the primary core integrity layer via the melt properties of the primary core integrity layer material will typically be effected using an on-line process in which the primary core integrity layer is substantially coincidentally formed and joined to a component during construction of the absorbent article. Thus, while the thermoplastic material of the primary core integrity layer is still in a liquefied/molten state sufficient to enable joinder, pressure is applied to the structures being joined in order to ensure good contact and adhesion between the primary core integrity layer and the component. As will be recognized by those skilled in the art, the process temperature and thus suitable thermoplastic materials should be selected to avoid damage to the component. Joinder of a primary core integrity layer formed of a thermoplastic, pressure-sensitive material can be effected in a like manner or, alternatively, via the pressure-sensitive properties of the thermoplastic material after solidification of the material.

In joining the primary core integrity layer to the component, it will usually be desired to minimize the pressure on the absorbent core in order to optimize the absorbent core integrity. In conventional diaper converting lines, the pressure can be minimized, e.g., by using a patterned combining roll, by varying the clearance between the combining rolls, and/or by using a vacuum conveyor belt.

E. Secondary Core Integrity Layer

The absorbent article, typically an absorbent article containing a multilayer absorbent core, can contain at least one additional absorbent core integrity layer, a secondary core integrity layer. The secondary core integrity layer functions in the manner of the primary core integrity layer to further enhance the absorbent core integrity. The secondary core integrity layer can be positioned in the absorbent article as described for the primary core integrity layer or adjacent the primary core integrity layer. Typically, the secondary core integrity layer will be positioned between adjacent layers of a multilayer absorbent core.

The secondary core integrity layer can have a size, shape, and dimensions such as those described for the primary core integrity layer. Thus, in one embodiment of the present invention, the surface area dimensions of the secondary core integrity layer are less than those of the absorbent core or one or more layers thereof. For example, each of the edges of the absorbent core or layer(s) thereof may extend beyond the periphery of the secondary core integrity layer. This embodiment may be preferred for industrial hygiene and/or economic reasons.

In an alternative embodiment of the present invention, the secondary core integrity layer has surface area dimensions such that it extends beyond at least a portion of at least one edge (side or end) of the absorbent core or, in a multilayer absorbent core, one or more layers thereof. Thus, the edge is enveloped between the secondary core integrity layer and a chassis component or another absorbent core layer. In this alternative embodiment, the secondary core integrity layer can extend beyond at least a portion of one or more the edges, more preferably the side edges, of the absorbent core or layer(s) thereof. This alternative embodiment may be preferred for enhanced absorbent core integrity. In a preferred embodiment of this aspect of the invention, the secondary core integrity layer is directly joined to a chassis component.

The size, shape, and/or dimensions of the secondary core integrity layer can be the same as or different from those of the primary core integrity layer or any additional core integrity layers. In addition, the extent of enveloping by the secondary core integrity layer can be the same as or different from that of the primary core integrity layer or any additional core integrity layer(s). Thus, the secondary core integrity layer can envelope relatively different portions of the edge(s) of an absorbent layer than enveloped by other core integrity layers.

As shown in FIG. 2, the surface area of the secondary core integrity layer 140 is less than the surface areas of each of the various absorbent layers of the absorbent core (more specifically, the (lateral) width of the secondary core integrity layer 140 is less than the (lateral) widths of each of the acquisition/distribution layer 150, tissue layer 170, and storage layer 190). Thus, the secondary core integrity layer 140 does not envelope the side edges 152, 172, and 192 of, respectively, acquisition/distribution layer 150, tissue layer 170, and storage layer 190.

The secondary core integrity layer can be formed of a thermoplastic material and by a process such as described for the primary core integrity layer. The secondary core integrity layer can be formed of the same thermoplastic material as the primary core integrity layer or from a different thermoplastic material. For ease of processing, the secondary core integrity layer is preferably formed of the same thermoplastic material as is the primary core integrity layer. In addition, the secondary core integrity layer can be formed using process parameters which are the same or different from those used to form the primary core integrity layer. In a preferred embodiment, the same process parameters are used for forming each core integrity layer in the absorbent article.

The secondary core integrity layer can be joined to one or more absorbent core layers and/or a chassis component in the manner described for the primary core integrity layer. For improving absorbent core integrity, the secondary core integrity layer is preferably directly joined to a chassis component. However, due to industrial hygiene concerns such direct joinder may not be preferred.

F. Other Components of the Absorbent Article

The diaper 20 can further comprise elasticized leg cuffs 32 for providing improved containment of liquids and other body exudates; an elastic waist feature 34 that provides improved fit and containment; elasticized side panels 30 to provide an elastically extensible feature that provides a more comfortable and contouring fit and more effective application of the diaper 20; and a fastening system 36 which forms a side closure which maintains the first waist region 56 and the second waist region 58 in an overlapping configuration such that lateral tensions are maintained around the circumference of the diaper to maintain the diaper on the wearer.

The elasticized leg cuffs 32 can be constructed in a number of different configurations, including those described in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989, each being incorporated herein by reference.

The elasticized waist feature comprises an elasticized waistband 35 that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels 30 may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. B1 4,662,875, issued to Hirotsu et al. on May 5, 1987; and U.S. Pat. No. 5,151,092, issued to Buell et al. on Sep. 29, 1992; each of which is incorporated herein by reference.

The diaper 20 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The tape tabs of the fastening system are then released from the release portion. The fastening system is then secured to the outer surface of the diaper to effect a side closure.

3. Alternative Types of Absorbent Articles

A primary core integrity layer and optionally one or more secondary core integrity layers can also be used consistent with the teachings herein in other types of absorbent articles, such as training pants, sanitary napkins, panty liners, adult incontinence devices and the like, to improve the dry/wet integrity thereof.

The term "training pant", as used herein, refers to disposable garments having fixed sides and leg openings. Training pants are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993.

The term "sanitary napkin", as used herein, refers to an article which is worn by females adjacent to the pudendal region that is intended to absorb and contain the various exudates which are discharged from the body (e.g., blood, menses, and urine). Suitable sanitary napkins that can be provided with the primary core integrity layer described herein are disclosed in U.S. Pat. No. 4,285,343, issued to McNair on Aug. 25, 1981; U.S. Pat. Nos. 4,589,876 and 4,687,478, issued to Van Tilburg on May 20, 1986 and Aug. 18, 1987 respectively; U.S. Pat. Nos. 4,917,697 and 5,007,906 issued to Osborn, et al. on Apr. 17, 1990 and Apr. 16, 1991, respectively; and U.S. Pat. Nos. 4,950,264 and 5,009,653 issued to Osborn on Aug. 21, 1990 and Apr. 23, 1991, respectively; in PCT International Publication No. WO 92/07535 published in the name of Visscher, et al. on May 14, 1992; and in PCT Patent Publication No. WO 93/01785 published Feb. 4, 1993 in the name of Osborn, et al.; and in U.S. patent application Ser. No. 07/966,240 (P&G Case 4750) filed in the name of Ahr, et al. on Oct. 26, 1992 (which also described other types of absorbent articles as well).

The terms "pantiliner" or "panty liner" refer to absorbent articles that are less bulky than sanitary napkins which are generally worn by women between their menstrual periods. Suitable absorbent articles in the form of pantiliners that can be provided with the primary core integrity layer described herein are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles that can be provided with the primary core integrity layer described herein are disclosed in U.S. Pat. No. 4,253,461 issued to Strickland, et al. on Mar. 3, 1981; U.S. Pat. Nos. 4,597,760 and 4,597,761 issued to Buell; the abovementioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. No. 07/637,090 filed by Noel, et al. on Jan. 3, 1991 (PCT Publication No. WO 92/11830 published on Jul. 23, 1992).

EXAMPLE 1

A disposable diaper is prepared having a primary core integrity layer and a secondary core integrity layer formed of an elastomeric, pressure-sensitive, hot-melt adhesive. The diaper comprises a thermally bonded polypropylene topsheet, a fluid impervious polyethylene backsheet and an absorbent core positioned between the topsheet and the backsheet. The side edges of the absorbent core are enveloped by the primary core integrity layer, which is directly joined to the topsheet and the backsheet.

The absorbent core comprises a modified hourglass-shaped storage layer positioned below a substantially rectangular-shaped acquisition/distribution layer and a rectangular-shaped, liquid pervious, wet-strength tissue sheet positioned therebetween. The secondary core integrity layer is positioned between the acquisition/distribution layer and the tissue layer.

The acquisition/distribution layer is an air laid web of stiffened, twisted, curled cellulose fibers made from Foley fluff (southern softwood kraft pulp, Buckeye Cellulose Corp., Memphis, Tenn., U.S.A.) and crosslinked with citric acid to the extent of about 3.8 mole percent citric acid on a dry fiber cellulose anhydroglucose basis as described in U.S. Pat. No. 5,137,537 (Herron et al.; Aug. 11, 1992). The fibers are airlaid to form a uniform web which is compressed with a hydraulic press to a density of 0.20 g/cc.

The storage layer comprises an air laid mixture of Foley fluff and sodium polyacrylate polymeric AGM particles of the type described in U.S. RE 32,649, reissued Apr. 19, 1988, and having an Absorbent Capacity of about 28 g/g. The storage layer has a fill layer which is a mixture of about 40% Foley fluff and about 60% AGM which is positioned adjacent the garment facing side of the tissue, and a dusting layer consisting essentially of the Foley fluff adjacent the fill layer. The fill layer has a width of about 10.7 cm (4.2") along the length of the storage layer. The storage layer comprises about 60% by weight Foley fluff and about 40% by weight AGM.

The acquisition/distribution layer has dimensions (width X length) of about 8.9 cm (3.5") (in the crotch region) by about 38.7 cm (15.25") and is positioned relative to the storage layer as shown in FIGS. 2 and 3. The storage layer has a minimum crotch width of about 10.7 cm (4.2"), a width at the ears of about 19.1 cm (7.5"), and a width at the rear (back) waist area of about 12.2 cm (4.8"). The tissue layer has dimensions of about 14.7 cm (5.8") X about 38.7 cm (15.25").

The secondary core integrity layer is formed on the acquisition/distribution layer by applying the adhesive H-2085 (Findley Adhesives, Inc.) directly onto the garment facing side of the acquisition/distribution layer using a J and M Laboratories 7.62 cm (3.0") meltblown glue gun designated AMBI-3.0-2 at an air pressure of 8 psi. (In forming each of the meltblown layers in this example, the meltblown adhesive materials are held at a temperature of 165° C. (330° F.); the gun temperature is 182° C. (360° F.); and the air temperature is 221° C. (430° F.)). The H-2085 adhesive is applied at a basis weight of 3.23 mg/in$^2$. A mesh is thus formed on the acquisition/distribution layer in the form of sinuous (wavy) strands of the H-2085 adhesive which are oriented in substantially the same direction with some crosswise linking so as to be intertwined. The strands have a denier of about 100 microns.

The secondary core integrity layer is then joined to the tissue layer by a layer of spiral HL-1258 adhesive (H. B. Fuller Co.) that is applied to the tissue. The spiral HL-1258 adhesive is applied to the tissue using a Nordson 3 spiral H200 glue gun with an air pressure of 20 psi at a basis weight of 3.1 mg/in$^2$. The resultant strands have a denier of about 25 microns.

The tissue layer is then joined to the storage layer by spiral HL-1258 adhesive applied to the garment facing side of the tissue. The spiral HL-1258 adhesive is applied to the garment facing side of the tissue using a Nordson 4 spiral glue gun with an air pressure of 20 psi at an HL-1258 adhesive basis weight of 2.1 mg/in$^2$; the resultant strands have a denier of about 25 microns.

The body facing side of the acquisition/distribution layer is then joined to the topsheet using a spiral pattern of the adhesive HL-1258 applied to the topsheet. 6 spirals are applied to the topsheet, the spirals having a width of 0.8" and 0.875" centers such that the HL-1258 adhesive has a basis weight of 2.00 mg/in$^2$.

The primary core integrity layer of meltblown H-2085 adhesive is then formed on the storage layer using a J and M Laboratories 15.24 cm (6.0") meltblown glue gun designated AMBI-6.0-4 with an air pressure of 8 psi at an H-2085 adhesive basis weight of 2.42 mg/in$^2$. The resultant mesh is in the form of sinuous (wavy) strands of the H-2085 adhesive which are oriented in substantially the same direction with some crosswise linking so as to be intertwined. The strands have a denier of about 100 microns.

The primary core integrity layer is then joined to the backsheet by fourteen (14) HL-1258 adhesive beads at an HL-1258 adhesive basis weight of 1.28 mg/in$^2$ and by spiral HL-1258 adhesive at a basis weight of 3.85 mg/in$^2$. The spiral HL-1258 adhesive is applied using a Nordson glue gun with an air pressure of 20 psi (strand denier will be about 25 microns); the HL-1258 adhesive beads are applied using a bead extruder.

The primary core integrity layer is then joined to the topsheet by HL-1258 adhesive applied to the topsheet. The topsheet and backsheet are then joined by HL-1258 adhesive applied to the backsheet. The finished diaper is packaged using a compressive force bagger with a compressive force of 1200 psi. The caliper of the finished diaper is about 0.53 cm (0.21").

EXAMPLE 2

A diaper is prepared as in Example 1 except that the fill layer has a basis weight gradient. The fill layer comprises about 15% of the AGM particles and about 80 to 85% of Foley fluff and has a basis weight gradient such that the front 60% of the storage layer has a basis weight of about 0.10–0.15 g/cm$^2$ (preferably 0.11 g/cm$^2$) and a density of about 0.13–0.20 g/cc (preferably 0.15 g/cc) and the rear 40% of the storage layer has a basis weight of about 0.03–0.05 g/cm$^2$ (preferably 0.04 g/cm$^2$) and a density of about 0.05–0.20 g/cc (preferably 0.06 g/cc). This storage layer is particularly useful as an absorbent core without an acquisition/distribution layer, in which case a secondary core integrity layer may be unnecessary.

EXAMPLE 3

A diaper is made as in Example 2, except that the storage layer has about 28% of the AGM particles and about 72% of Foley fluff. The storage layer has a basis weight gradient as described in Example 2.

EXAMPLES 4–6

Examples 4–6 are made in the same manner as Examples 1–3, except that the bagger force is 700 psi.

EXAMPLE 7

A disposable diaper having a primary core integrity layer and a secondary core integrity layer formed of a high wet strength adhesive is prepared. The diaper has a topsheet, backsheet, and absorbent core having an acquisition/distribution layer and a storage layer as described in Example 1.

The secondary core integrity layer is formed on the acquisition/distribution layer by applying the adhesive HL-1262 (H. B. Fuller Co.) directly onto the garment facing side of the acquisition/distribution layer using a J and M Laboratories 7.62 cm (3.0") meltblown glue gun designated AMBI-3.0-2 at an air pressure of 1 to 4 psi. (In forming each of the meltblown layers in this example, the meltblown adhesive materials are held at a temperature of 305° F.; the gun temperature is 340° F.; and the air temperature is 380° F. The HL-1262 adhesive is applied at a basis weight of 3.23 mg/in$^2$. A mesh is thus formed on the acquisition/distribution layer in the form of sinuous (wavy) strands of the HL-1262 adhesive which are oriented in substantially the same direction with at least some crosswise linking so as to be intertwined. The strands have a denier of about 100 microns.

The secondary core integrity layer is then joined to the tissue layer by a layer of spiral HL-1258 adhesive (H. B. Fuller Co.) which is applied to the tissue. The HL-1258 adhesive is applied to the tissue using a glue gun designated H200, available from Nordson Co., with an air pressure of 20 psi at a basis weight of 3.1 mg/in$^2$. The resultant strands have a denier of about 25 microns.

The tissue layer is then joined to the storage layer by 4 substantially parallel spirals of HL-1258 adhesive applied to the garment facing side of the tissue. The HL-1258 adhesive is applied to the garment facing side of the tissue using an H200 glue gun with an air pressure of 20 psi at an HL-1258 adhesive basis weight of 2.1 mg/in$^2$; the resultant strands have a denier of about 25 microns.

The body facing side of the acquisition/distribution layer is then joined to the topsheet using a spiral pattern of the adhesive HL-1258 applied to the topsheet. 6 spirals are applied to the topsheet, the spirals having a width of 0.8" and 0.875" centers such that the HL-1258 adhesive has a basis weight of 2.00 mg/in$^2$.

A primary core integrity layer of meltblown HL-1262 adhesive is then formed on the storage layer using a J and M Laboratories 15.24 cm (6.0") meltblown glue gun designated AMBI-6.0-4 with an air pressure of from 1 to 4 psi at an HL-1262 adhesive basis weight of 2.42 mg/in$^2$. The resultant mesh is in the form of sinuous (wavy) strands of the HL-1262 adhesive which are oriented in substantially the same direction with some crosswise linking so as to be intertwined. The strands have a denier of about 100 microns.

The primary core integrity layer is then joined to the backsheet by fourteen (14) HL-1262 adhesive beads at an HL-1262 adhesive basis weight of 1.28 mg/in$^2$ and by spiral HL-1258 adhesive at a basis weight of 3.85 mg/in$^2$. The spiral HL-1258 adhesive is applied using an H200 Nordson glue gun with an air pressure of 20 psi (strand denier will be about 25 microns); the HL-1262 adhesive beads are applied using a bead extruder.

The primary core integrity layer is then joined to the topsheet by HL-1258 spiral adhesive applied to the topsheet. The topsheet and backsheet are then joined by beads of HL-1258 adhesive applied to the backsheet. The finished diaper is packaged using a compressive force bagger with a compressive force of 1200 psi. The caliper of the finished diaper is about 0.53 cm (0.21").

Examples 1–7 will exhibit improved absorbent core integrity, including reduced slumping, reduced roping, and reduced tearing in the crotch region (both along the lateral crotch fold lines and elsewhere), particularly tearing of the acquisition/distribution layer. This absorbent core integrity improvement leads to increased absorbent core utilization, particularly since diapers containing acquisition/distribution layers torn in the fold area have a lower probability of containing urine past the fold line than diapers that are not torn. Examples using a lower bagger force as a single variable would is tend to have greater absorbent core integrity relative to examples made with higher bagger forces, particularly a reduction in tearing along the lateral crotch fold line of the diapers. Example 7, having a primary core integrity layer and a secondary core integrity layer formed of a high wet strength adhesive, tends to have improved absorbent core integrity when wet, relative to Example 1.

The absorbent core integrity is determined by tearing grade, roping grade, and percent urine past fold line. These in turn are evaluated by comparing a dry diaper to a diaper wetted in actual use only by urine of a known urine loading.

The roping grade is determined by visually inspecting the absorbent core crotch region using a "light box" such as are known in the art. The absorbent core width of the used diaper is compared to that of the unused diaper. A negative change in width after use may be indicative of some degree of roping, with greater negative changes indicating higher degrees of roping. The change in width is apparent by bunching of the absorbent core. The bunching results in a change in softness and/or stiffness of the absorbent core as a result of packing/matting of the absorbent core material. The absorbent cores are graded on a scale of 1–4 as follows:

1. Severe bunching—absorbent core is hard and stiff.
2. Moderate bunching—absorbent core is hard but still pliable.
3. Slight bunching—absorbent core starts to mat.
4. No roping.

Absorbent core tearing grade is determined by visual inspection of the entire absorbent core for cracks and tears. The more tears, the lower the grade, with all tears in the crotch area being weighted more heavily than tears outside the crotch area. The absorbent cores are graded on a scale of 14 as follows:

1. Severe tearing—tears separate the crotch along the lateral fold line and/or are longer than 6 cm outside the crotch area.
2. Moderate tearing—tears half separate the crotch along the lateral fold line and/or are between 3 and 6 cm long outside the crotch area.
3. Slight tearing—tears in the crotch are less than 2 cm long and less than 3 cm outside the crotch area.
4. No tears.

The percent of urine past fold line is indicative of breakage of the absorbent core in the region of the lateral crotch fold line. This percentage is determined by cutting the wetted diaper along the fold line. The rear portion (worn toward the back of the wearer's body) is weighed. The weight of the rear portion is divided by the weight of the entire wetted diaper and multiplied by 100 to obtain the percent urine past fold line.

Absorbent core slumping is indicative of slippage between, and/or separation of, the absorbent core (or component thereof) and a chassis component (and/or another absorbent core component). Slumping may indicate a loss of adhesion between a fibrous absorbent core component and the glue bonding the fibrous component to the topsheet or to another fibrous absorbent core component. Slumping is determined visually by using a "light box."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a) a liquid pervious topsheet;
   b) a liquid impervious backsheet joined to said topsheet;
   c) an absorbent core comprising one or more absorbent layers comprising hydrophilic fibers, said absorbent core and layers thereof having side edges and end edges, said absorbent core being positioned between said topsheet and said backsheet; and
   d) a primary core integrity layer comprising a continuous mesh of strands of thermoplastic material in substantially random orientation and having adhesive properties, said primary core integrity layer enveloping at least a portion of one of said edges of at least one of said absorbent layers and being joined to said topsheet by the adhesive properties of said primary core integrity layer, said primary core integrity layer being positioned between said absorbent core and said backsheet; wherein said thermoplastic material is a hot-melt, high wet strength adhesive having a Wet Peel Strength of at least about 4 g/cm.

2. An absorbent article comprising:
   a) a liquid pervious topsheet;
   b) a liquid impervious backsheet joined to said topsheet;
   c) an absorbent core comprising one or more absorbent layers comprising hydrophilic fibers, said absorbent core and layers thereof having side edges and end edges, said absorbent core being positioned between said topsheet and said backsheet; and
   d) a primary core integrity layer comprising a continuous mesh of strands of thermoplastic material in substantially random orientation and having adhesive properties, said primary core integrity layer enveloping at least a portion of one of said edges of at least one of said absorbent layers and being joined to said topsheet by the adhesive properties of said primary core integrity layer, said primary core integrity layer being positioned between said absorbent core and said backsheet; wherein said thermoplastic material is a hot-melt, elastomeric, pressure-sensitive adhesive.

3. An absorbent article comprising:

a) a liquid pervious topsheet;

b) a liquid impervious backsheet joined to said topsheet;

c) an absorbent core comprising hydrophilic fibers, said absorbent core being positioned between said topsheet and said backsheet; wherein said absorbent core comprises an upper acquisition/distribution layer and a lower storage layer, said absorbent core having side edges and end edges; and d) a primary core integrity layer comprising a continuous mesh of strands of thermoplastic material in substantially random orientation and having adhesive properties, said primary core integrity layer enveloping at least a portion of one of said edges of at least one of said absorbent layers and being joined to said topsheet and said backsheet by the adhesive properties of said primary core integrity layer, said primary core integrity layer being positioned between said absorbent core and said backsheet.

4. The absorbent article of claim 3 wherein said primary core integrity layer is positioned between said storage layer and said backsheet and envelopes at least a portion of one of said edges of said storage layer.

5. The absorbent article of claim 4 additionally comprising a secondary core integrity layer comprising a continuous mesh of strands of thermoplastic material in substantially random orientation positioned between said acquisition/distribution layer and said storage layer.

6. The absorbent article of claim 5 additionally comprising a tissue layer positioned between said secondary core integrity layer and said storage layer.

7. The absorbent article of claim 5 wherein said thermoplastic material of said primary core integrity layer and of said secondary core integrity layer is a hot-melt, high wet strength adhesive having a Wet Peel Strength of at least about 4 g/cm according to the Peel Test.

8. The absorbent article of claim 5 wherein said thermoplastic material of said primary core integrity layer and of said secondary core integrity layer is a hot-melt, elastomeric, pressure-sensitive adhesive.

* * * * *

UNITED STATES PATENT AND TRADEMARK OFFICE
CERTIFICATE OF CORRECTION

PATENT NO. : 5,833,678
DATED : November 10, 1998
INVENTOR(S) : GREGORY ASHTON, ET AL.

It is certified that error appears in the above-identified patent and that said Letters Patent is hereby corrected as shown below:

*Column 12, line 47, "Exian" should read --Exlan--.*

*Colunm 14, line 5, "are" should read --an--.*

*Column 15, line 38, "abovereferenced" should read --above referenced--.*

*Column 18, line 38, "Will" should read --will--.*

*Column 27, line 25, please delete the comma after the word "might".*

*Column 27, line 31, "welt" should read --wet--.*

*Column 32, lines 8 and 9, "abovementioned" should read --above mentioned--.*

Column 35, line 61, "14" should read 1-4--

*Column 36, line 48, "4 g/cm" should read --4 g/in--.*

*Column 38, line 16, "4 g/cm" should read --4 g/in--.*

Signed and Sealed this

Twenty-fourth Day of October, 2000

Attest:

Q. TODD DICKINSON

*Attesting Officer*     *Director of Patents and Trademarks*